(12) United States Patent
Kanazawa et al.

(10) Patent No.: US 11,345,914 B2
(45) Date of Patent: May 31, 2022

(54) COMPOSITION FOR DELIVERING NUCLEIC ACID AND NUCLEIC ACID-CONTAINING COMPOSITION

(71) Applicant: TOKYO UNIVERSITY OF PHARMACY AND LIFE SCIENCES, Hachioji (JP)

(72) Inventors: Takanori Kanazawa, Hachioji (JP); Yuuki Takashima, Hachioji (JP); Hisako Ibaraki, Hachioji (JP); Shunsuke Shiraishi, Hachioji (JP); Ei Nakata, Hachioji (JP); Yusuke Iriyama, Funabashi (JP); Keiichiro Otsuka, Shiraoka (JP)

(73) Assignee: TOKYO UNIVERSITY OF PHARMACY AND LIFE SCIENCES, Hachioji (JP)

( * ) Notice: Subject to any disclaimer, the term of this patent is extended or adjusted under 35 U.S.C. 154(b) by 0 days.

(21) Appl. No.: 16/629,511

(22) PCT Filed: Jul. 11, 2018

(86) PCT No.: PCT/JP2018/026199
§ 371 (c)(1),
(2) Date: May 5, 2020

(87) PCT Pub. No.: WO2019/013255
PCT Pub. Date: Jan. 17, 2019

(65) Prior Publication Data
US 2021/0115440 A1 Apr. 22, 2021

(30) Foreign Application Priority Data
Jul. 11, 2017 (JP) .............................. JP2017-135547

(51) Int. Cl.
| | | |
|---|---|---|
| *C07H 21/04* | (2006.01) |
| *C12N 15/113* | (2010.01) |
| *A61K 9/107* | (2006.01) |
| *A61K 9/14* | (2006.01) |
| *A61K 31/7105* | (2006.01) |
| *A61K 31/713* | (2006.01) |
| *A61K 47/34* | (2017.01) |
| *A61K 47/42* | (2017.01) |

(52) U.S. Cl.
CPC .......... *C12N 15/113* (2013.01); *A61K 9/1075* (2013.01); *A61K 9/14* (2013.01); *A61K 31/713* (2013.01); *A61K 31/7105* (2013.01); *A61K 47/34* (2013.01); *A61K 47/42* (2013.01); *C12N 2310/11* (2013.01); *C12N 2310/141* (2013.01); *C12N 2310/3183* (2013.01)

(58) Field of Classification Search
CPC .................................................... C12N 15/113
See application file for complete search history.

(56) References Cited

U.S. PATENT DOCUMENTS 9,439,858 B2 * 9/2016 Kim ..................... A61K 31/365
2011/0268772 A1 11/2011 Kim et al.
2012/0149649 A1 6/2012 Kato et al.

FOREIGN PATENT DOCUMENTS

JP 2011-173802 A 9/2011
JP 2012-513460 A 6/2012

OTHER PUBLICATIONS

Liu et al. (International Journal of Nanomedicine, 2017, 12, 3561-3575).*
Zhou et al. (Biomaterials, 24, 2003, 3563-3570).*
Wang et al. (Journal of Controlled Release, 166, 2013, 106-114).*
Farkhani et al. (Peptides, 57, 2014, 78-94).*
Deng et al., "A biodegradable triblock copolymer poly(ethylene glycol)-b-poly($_L$-lactide)-b-poly($_L$-lysine): Synthesis, self-assembly, and RGD peptide modification," *Polymer*, 48(1): 139-149 (2007).
Liu et al., "cNGR conjugated poly(lactic acid)-poly(ethylene glycol) nanoparticles for targeted gene delivery," *J. Control. Release*, 152(Suppl. 1): e155-e157 (2011).
Tanaka et al., "Cytoplasm-responsive nanocarriers conjugated with a functional cell-penetrating peptide for systemic siRNA delivery," *Int. J. Pharm.*, 455(1-2): 40-47 (2013).
Zhao et al., "Self-assembly nanomicelles based on cationic mPEG-PLA-b-Polyarginine($R_{15}$) triblock copolymer for siRNA delivery," *Biomaterials*, 33(28): 6793-6807 (2012).
Japanese Patent Office, International Search Report in International Patent Application No. PCT/JP2018/026199 (dated Oct. 16, 2018).

* cited by examiner

*Primary Examiner* — Amy H Bowman
(74) *Attorney, Agent, or Firm* — Leydig, Voit & Mayer, Ltd.

(57) ABSTRACT

This is to provide a composition for delivering a nucleic acid and a nucleic acid-containing composition which ensure stability of a nucleic acid drug, have a high intracellular introduction rate, can efficiently express the function of a nucleic acid drug, and have low cytotoxicity.
Disclosed is a composition for delivering a nucleic acid and a nucleic acid-containing composition each comprises a block copolymer in which a polyethylene glycol segment and a hydrophobic polyester segment are linked, and a peptide having 4 to 30 residues containing at least one selected from the group consisting of arginine and lysine.

21 Claims, 9 Drawing Sheets
Specification includes a Sequence Listing.

siRNA only siRNA/peptide/MPEG-PCL

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 1
ccaugaagcc cuggagugct t                                              21

<210> SEQ ID NO 2
<211> LENGTH: 21
```

```
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 2
gcacuccagg gcuucaucgt t                                                 21

<210> SEQ ID NO 3
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 3
ggugcagaaa gaagacauut t                                                 21

<210> SEQ ID NO 4
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 4
aaugucuucu uucugcacct t                                                 21

<210> SEQ ID NO 5
<211> LENGTH: 18
<212> TYPE: RNA
<213> ORGANISM: Artificial Sequence
<220> FEATURE:
<223> OTHER INFORMATION: si RNA
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (18)..(18)
<223> OTHER INFORMATION: um

<400> SEQUENCE: 5
agaucacccu ccuuaaau                                                     18

<210> SEQ ID NO 6
<211> LENGTH: 21
<212> TYPE: RNA
<213> ORGANISM: Artificial Sequence
<220> FEATURE:
<223> OTHER INFORMATION: si RNA
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (17)..(17)
<223> OTHER INFORMATION: um
```

-continued

<400> SEQUENCE: 6
uauuuaagga gggugaucuu u                                                 21

<210> SEQ ID NO 7
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 7
auccgcgcga uaguacguat t                                                 21

<210> SEQ ID NO 8
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 8
uacguacuau cgcgcggaut t                                                 21

<210> SEQ ID NO 9
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 9
cuuacgcuga guacuucgat t                                                 21

<210> SEQ ID NO 10
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 10
ucgaaguacu cagcguaagt t                                                 21

<210> SEQ ID NO 11
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

<400> SEQUENCE: 11
cuuacgcuga guacuucgat t                                                 21

<210> SEQ ID NO 12
<211> LENGTH: 21
<212> TYPE: DNA
<213> ORGANISM: Artificial Sequence
<220> FEATURE:
<223> OTHER INFORMATION: si RNA or Combined DNA/RNA Molecule: 19-base
      RNA combined with 2-base DNA

```
<400> SEQUENCE: 12
ucgaaguacu cagcguaagt t                                              21

<210> SEQ ID NO 13
<211> LENGTH: 10
<212> TYPE: PRT
<213> ORGANISM: Artificial Sequence
<220> FEATURE:
<223> OTHER INFORMATION: peptide modified by N-terminal stearoylation
<220> FEATURE:
<221> NAME/KEY: LIPID
<222> LOCATION: (1)..(1)

<400> SEQUENCE: 13

Cys His His Arg Arg Arg Arg His His Cys
1               5                   10

<210> SEQ ID NO 14
<211> LENGTH: 8
<212> TYPE: PRT
<213> ORGANISM: Artificial Sequence
<220> FEATURE:
<223> OTHER INFORMATION: peptide modified by N-terminal stearoylation
<220> FEATURE:
<221> NAME/KEY: LIPID
<222> LOCATION: (1)..(1)

<400> SEQUENCE: 14

His His Arg Arg Arg Arg His His
1               5

<210> SEQ ID NO 15
<211> LENGTH: 8
<212> TYPE: PRT
<213> ORGANISM: Artificial Sequence
<220> FEATURE:
<223> OTHER INFORMATION: peptide modified by N-terminal stearoylation
<220> FEATURE:
<221> NAME/KEY: LIPID
<222> LOCATION: (1)..(1)

<400> SEQUENCE: 15

His His His His Arg Arg Arg Arg
1               5

<210> SEQ ID NO 16
<211> LENGTH: 8
<212> TYPE: PRT
<213> ORGANISM: Artificial Sequence
<220> FEATURE:
<223> OTHER INFORMATION: peptide modified by N-terminal stearoylation
<220> FEATURE:
<221> NAME/KEY: LIPID
<222> LOCATION: (1)..(1)

<400> SEQUENCE: 16

Arg Arg Arg Arg His His His His
1               5

<210> SEQ ID NO 17
<211> LENGTH: 8
<212> TYPE: PRT
<213> ORGANISM: Artificial Sequence
<220> FEATURE:
<223> OTHER INFORMATION: peptide modified by N-terminal stearoylation
<220> FEATURE:
<221> NAME/KEY: LIPID
<222> LOCATION: (1)..(1)
```

<400> SEQUENCE: 17

His Arg His Arg His Arg His Arg
1               5

<210> SEQ ID NO 18
<211> LENGTH: 10
<212> TYPE: PRT
<213> ORGANISM: Artificial Sequence
<220> FEATURE:
<223> OTHER INFORMATION: peptide

<400> SEQUENCE: 18

Cys His His Arg Arg Arg Arg His His Cys
1               5                   10

<210> SEQ ID NO 19
<211> LENGTH: 9
<212> TYPE: PRT
<213> ORGANISM: Artificial Sequence
<220> FEATURE:
<223> OTHER INFORMATION: peptide

<400> SEQUENCE: 19

Gly His His Arg Arg Arg Arg His His
1               5

<210> SEQ ID NO 20
<211> LENGTH: 10
<212> TYPE: PRT
<213> ORGANISM: Artificial Sequence
<220> FEATURE:
<223> OTHER INFORMATION: peptide modified by N-terminal stearoylation
<220> FEATURE:
<221> NAME/KEY: LIPID
<222> LOCATION: (1)..(1)

<400> SEQUENCE: 20

Cys His His Lys Lys Lys Lys His His Cys
1               5                   10

<210> SEQ ID NO 21
<211> LENGTH: 14
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: phosphorothioate bond between nucleosides
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (14)..(14)
<223> OTHER INFORMATION: m5c

<400> SEQUENCE: 21
tcagtcatga cttc                                                       14

```
<210> SEQ ID NO 22
<211> LENGTH: 13
<212> TYPE: DNA
<213> ORGANISM: Artificial Sequence
<220> FEATURE:
<223> OTHER INFORMATION: DNA/RNA heteroduplex oligonucleotide (HDO)
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: phosphorothioate bond between nucleosides
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c

<400> SEQUENCE: 22
gcattggtat tca                                                      13

<210> SEQ ID NO 23
<211> LENGTH: 13
<212> TYPE: RNA
<213> ORGANISM: Artificial Sequence
<220> FEATURE:
<223> OTHER INFORMATION: DNA/RNA heteroduplex oligonucleotide (HDO)
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: phosphorothioate bond between nucleosides
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (11)..(13)
<223> OTHER INFORMATION: phosphorothioate bond between nucleosides
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: cm

<400> SEQUENCE: 23
ugaauaccaa ugc                                                      13

<210> SEQ ID NO 24
<211> LENGTH: 30
<212> TYPE: DNA
<213> ORGANISM: Artificial Sequence
<220> FEATURE:
<223> OTHER INFORMATION: single stranded DNA/RNA heteroduplex
```

```
            oligonucleotide (ss-HDO)
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: phosphorothioate bond between nucleosides
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (18)..(19)
<223> OTHER INFORMATION: LNA
<220> FEATURE:
<221> NAME/KEY: modified_base
<222> LOCATION: (18)..(30)
<223> OTHER INFORMATION: phosphorothioate bond between nucleosides
<220> FEATURE:
<221> NAME/KEY: modified_base
<222> LOCATION: (19)..(19)
<223> OTHER INFORMATION: m5c
<220> FEATURE:
<221> NAME/KEY: modified_base
<222> LOCATION: (28)..(30)
<223> OTHER INFORMATION: LNA
<220> FEATURE:
<221> NAME/KEY: modified_base
<222> LOCATION: (29)..(29)
<223> OTHER INFORMATION: m5c

<400> SEQUENCE: 24
ugaauaccaa ugcaaaagca ttggtattca                                    30

<210> SEQ ID NO 25
<211> LENGTH: 5
<212> TYPE: PRT
<213> ORGANISM: Artificial Sequence
<220> FEATURE:
<223> OTHER INFORMATION: peptide

<400> SEQUENCE: 25

Cys His His Arg Arg
1               5

<210> SEQ ID NO 26
<211> LENGTH: 8
<212> TYPE: PRT
<213> ORGANISM: Artificial Sequence
<220> FEATURE:
<223> OTHER INFORMATION: peptide

<400> SEQUENCE: 26

His His Arg Arg Arg Arg His His
1               5

<210> SEQ ID NO 27
<211> LENGTH: 8
<212> TYPE: PRT
<213> ORGANISM: Artificial Sequence
<220> FEATURE:
<223> OTHER INFORMATION: peptide

<400> SEQUENCE: 27

His His His His Arg Arg Arg Arg
```

```
<210> SEQ ID NO 28
<211> LENGTH: 8
<212> TYPE: PRT
<213> ORGANISM: Artificial Sequence
<220> FEATURE:
<223> OTHER INFORMATION: peptide

<400> SEQUENCE: 28

Arg Arg Arg Arg His His His His
1               5
```

COMPOSITION FOR DELIVERING NUCLEIC ACID AND NUCLEIC ACID-CONTAINING COMPOSITION

CROSS-REFERENCE TO RELATED APPLICATIONS

This patent application is the U.S. national phase of International Patent Application No. PCT/JP2018/026199, filed Jul. 11, 2018, which claims the benefit of Japanese Patent Application No. 2017-135547, filed on Jul. 11, 2017, which are incorporated by reference in their entireties herein.

TECHNICAL FIELD

The present invention relates to a carrier composition for delivering a nucleic acid, in particular, siRNA into cells of a target diseased part, and a nucleic acid-containing composition using the same.

BACKGROUND ART

Nucleic acid drugs can treat diseases by directly acting on the causative molecules of the disease, so that they are expected to be an effective treatment method even for diseases that the effects cannot be expected with conventional small molecule drugs such as enzyme inhibitors, etc.

However, nucleic acids such as siRNA, etc., are easily degraded and unstable in blood, so that for applying these to a wide range of diseases as nucleic acid drugs, it has been desired to develop a method capable of administering into blood and efficiently delivering to a target tissue by systemic administration.

As a delivery system of a nucleic acid drug, a method of using a polymer carrier has been reported. For example, it has been reported a delivery system of siRNA which uses a polymer obtained by conjugating a block copolymer (hereinafter referred to as MPEG-PCL) comprising a methoxy-polyethylene glycol segment (hereinafter referred to as MPEG) and a poly(ε-caprolactone) segment (hereinafter referred to as PCL), and a peptide having 10 residues which comprise cysteine, histidine and arginine (for example, see Non-Patent Document 1). It has been reported that the nucleic acid delivery system has a micellar structure having a hydrophobic PCL as a core, and siRNA is supported on the micelle by electrostatic interaction with a positively charged peptide, thereby both of stability in blood and intracellular uptake ability can be accomplished, and in the study of using a cancer-bearing model mouse, a high therapeutic effect can be obtained.

PRIOR ART DOCUMENTS

Non-Patent Documents

Non-Patent Document 1: International Journal of Pharmaceutics, vol. 455, pp. 40-47 (2013)

SUMMARY OF THE INVENTION

Problems to be Solved by the Invention

In a nucleic acid drug which express its function by administration in a blood, it has been desired to obtain a composition for delivering a nucleic acid and a nucleic acid-containing composition, in which stability of the nucleic acid drug is ensured, and the intracellular introduction rate is high, the function of the nucleic acid drug can be efficiently expressed, and cytotoxicity is low. In particular, a composition for delivering a nucleic acid and a nucleic acid-containing composition which can be applied to short strand nucleic acid drugs such as siRNA have been required.

An object of the present invention is to provide a composition for delivering a nucleic acid and a nucleic acid-containing composition which have low cytotoxicity and accomplish high therapeutic efficacy.

Means to Solve the Problems

The present inventors have conducted studies based on Non-Patent Document 1 using a polymer obtained by conjugating MPEG-PCL and a peptide, but cytotoxicity caused by the polymer micelle was confirmed.

Thereafter, the present inventors have earnestly studied to solve the above-mentioned problems, and as a result, they have found that, instead of conjugating a peptide to MPEG-PCL, an electrostatic interaction complex of a positively charged peptide having a fat-soluble group and siRNA is contained inside of a micelle by a manner of a non-covalent bond, good intracellular transducing effect of the nucleic acid molecule is exhibited without exhibiting cytotoxicity, and a high therapeutic effect can be obtained in vivo, whereby accomplished the present invention. That is, the present invention includes the following embodiments.

1. A composition for delivering a nucleic acid which comprises a block copolymer in which a polyethylene glycol segment and a hydrophobic polyester segment are linked, and a peptide having 4 to 30 residues containing at least one amino acid selected from the group consisting of arginine and lysine.
2. The composition for delivering a nucleic acid described in 1., wherein the above-mentioned peptide contains a fat-soluble group directly or through a bonding group.
3. The composition for delivering a nucleic acid described in 2., wherein the above-mentioned fat-soluble group is a group selected from the group consisting of a (C4 to C30) linear, branched or cyclic alkyl group which may have a substituent(s), a (C4 to C30) linear, branched or cyclic alkenyl group which may have a substituent(s), and a (C7 to C30) linear or branched aralkyl group which may have a substituent(s).
4. The composition for delivering a nucleic acid described in any one of 1. to 3., wherein the above-mentioned peptide further contains histidine.
5. The composition for delivering a nucleic acid described in any one of 1. to 4., wherein the above-mentioned peptide contains arginine and histidine.
6. The composition for delivering a nucleic acid described in 5., wherein a total number of an arginine residue and a histidine residue in the above-mentioned peptide is 50 to 100% based on a total number of all residues of the peptide.
7. The composition for delivering a nucleic acid described in any one of 1. to 6., wherein the above-mentioned block copolymer is a polyethylene glycol-poly(ε-caprolactone), a polyethylene glycol-poly(lactic acid-glycolic acid copolymer) or a polyethylene glycol-polylactic acid.
8. The composition for delivering a nucleic acid described in any one of 1. to 7., wherein the above-mentioned block copolymer is a polyethylene glycol-poly(ε-caprolactone).
9. The composition for delivering a nucleic acid described in any one of 1. to 8., wherein the above-mentioned block copolymer and the above-mentioned peptide form a particle.

10. The composition for delivering a nucleic acid described in 9., wherein a particle diameter of the above-mentioned particle is 50 nm or less.

11. A method for manufacturing the composition for delivering a nucleic acid described in any one of 1. to 10., which comprises the steps of mixing a water-soluble organic solvent solution of a block copolymer in which a polyethylene glycol segment and a hydrophobic polyester segment are linked, and an aqueous solution of a peptide having 4 to 30 residues containing at least one amino acid selected from the group consisting of arginine and lysine, and then, removing the organic solvent.

12. A nucleic acid-containing composition wherein the composition for delivering a nucleic acid described in any one of 1. to 8. contains a nucleic acid.

13. The nucleic acid-containing composition wherein the composition for delivering a nucleic acid described in 9. or 10. is a nucleic acid-containing composition containing a nucleic acid, and the above-mentioned nucleic acid forms a particle with a block copolymer and a peptide.

14. The nucleic acid-containing composition described in 13., wherein a particle size of the above-mentioned particle is 50 nm or less.

15. The nucleic acid-containing composition described in any one of 12. to 14., wherein the above-mentioned nucleic acid is RNA utilizing RNA interference or an antisense nucleic acid.

16. The nucleic acid-containing composition described in any one of 12. to 15., wherein the above-mentioned nucleic acid is siRNA or miRNA.

17. A method for manufacturing the nucleic acid-containing composition described in any one of 12. to 16., which comprises the steps of mixing a water-soluble organic solvent solution of a block copolymer in which a polyethylene glycol segment and a hydrophobic polyester segment are linked, and an aqueous solution of a peptide having 4 to 30 residues containing at least one amino acid selected from the group consisting of arginine and lysine, and after removing the organic solvent, mixing a nucleic acid(s).

18. A nucleic acid-containing composition wherein the nucleic acid-containing composition described in any one of the above-mentioned 12. to 16. further contains a low-molecular weight drug.

19. A kit for delivering a nucleic acid which comprises the composition for delivering a nucleic acid described in any one of the above-mentioned 1. to 10.

20. A kit for delivering a nucleic acid which comprises a first composition containing a block copolymer in which a polyethylene glycol segment and a hydrophobic polyester segment are linked, and a second composition containing a peptide having 4 to 30 residues containing at least one amino acid selected from the group consisting of arginine and lysine.

21. A pharmaceutical composition which comprises the nucleic acid-containing composition described in any one of the above-mentioned 12. to 16. and 18. as an effective ingredient.

Effects of the Invention

According to the present invention, there are provided a composition for delivering a nucleic acid and a nucleic acid-containing composition that have low cytotoxicity and realize high therapeutic efficacy.

EMBODIMENTS TO CARRY OUT THE INVENTION

Figure 1:
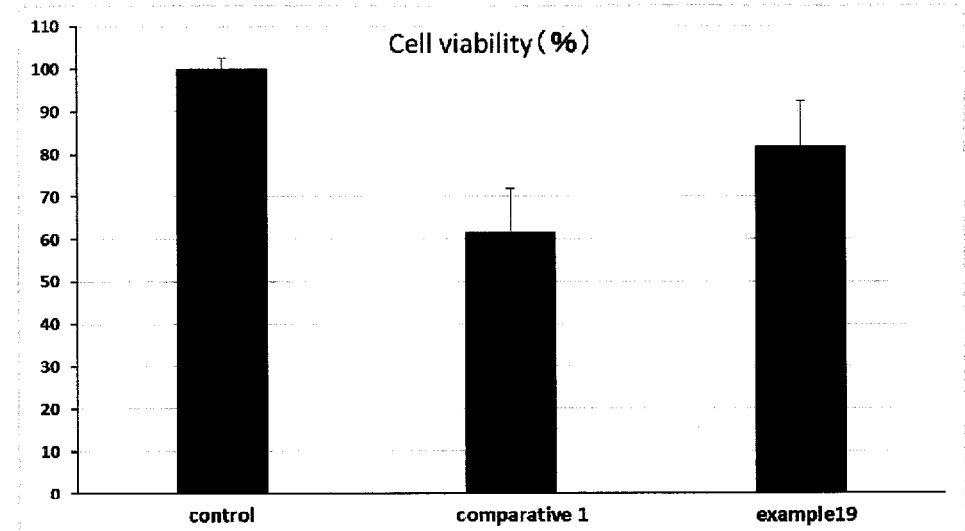
FIG. 1 is a graph showing cell viability of mouse macrophage cell line-like cells with regard to the nucleic acid-containing composition according to the present embodiment.

The present invention relates to a composition for delivering a nucleic acid which is for delivering a nucleic acid molecule to a target tissue and a target cell, which is a composition containing a block copolymer of a polyethylene glycol segment and a hydrophobic polyester segment, and a peptide having 4 to 30 residues containing at least one selected from arginine and lysine. Further, it relates to a nucleic acid-containing composition containing a nucleic acid. In the following, details of the present invention are explained.

First, the terms to be used for the description of the chemical structure in the present specification are explained.

Incidentally, in the present invention, "n-" means normal, "i-" means iso, "s-" means secondary, and "t-" means tertiary.

The terms "a group derived from" mean a group in which a hydrogen atom at an arbitrary position is removed from the objective molecule.

The terms "may have a substituent(s)" mean unsubstituted, or substituted by at least one substituent.

The "halogen atom" means a fluorine atom, a chlorine atom, a bromine atom or an iodine atom.

The linear, branched or cyclic alkyl group is a linear, branched or cyclic saturated hydrocarbon group and, for example, there may be mentioned, as specific examples, a methyl group, an ethyl group, an n-propyl group, an i-propyl group, an n-butyl group, an i-butyl group, an s-butyl group, an t-butyl group, an n-pentyl group, a cyclopentyl group, an n-hexyl group, a cyclohexyl group, a cyclohexylmethyl group, a cyclohexylethyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, an isooctyl group, an isodecyl group, an isododecyl group, an isotetradecyl group, an isohexadecyl group, an isooctadecyl group, a t-octyl group, a t-decyl group, a t-dodecyl group, a t-tetradecyl group, a t-hexadecyl group, a t-octadecyl group, etc.

In the present specification, the (Ca to Cb) linear, branched or cyclic alkyl group is the above-mentioned linear, branched or cyclic alkyl group having a to b carbon atoms, and each selected in the range of the specified number of carbon atoms from the examples of the above-mentioned linear, branched or cyclic alkyl groups.

In the present specification, the linear or branched alkyl group is a linear or branched saturated hydrocarbon group, and specific examples thereof are included in the above-mentioned linear, branched or cyclic alkyl group. Incidentally, the cyclic alkyl group is not included in a linear or branched saturated hydrocarbon group. In the present specification, the (Ca to Cb) linear or branched alkyl group is the above-mentioned linear or branched alkyl group having a to b carbon atoms, and each selected in the range of the specified number of carbon atoms from the examples of the above-mentioned linear or branched alkyl group.

The linear, branched or cyclic alkenyl group is a linear, branched or cyclic unsaturated hydrocarbon group having a carbon-carbon double bond in at least any of a portion and may be mentioned, for example, a 1-propenyl group, a 1-butenyl group, a 2-methyl-2-butenyl group, a 2-methyl-1,3-butadienyl group, a 1-octenyl group, a 1-decenyl group, a 1-dodecenyl group, a 1-tetradecenyl group, a 1-hexadecenyl group, a 1-cyclohexenyl group, a 3-cyclohexenyl group, a 1-octadecenyl group, a cis-9-octadecenyl group, a 9-hexadecenyl group, etc.

In the present specification, the (Ca to Cb) linear, branched or cyclic alkenyl group is the above-mentioned linear, branched or cyclic alkenyl group having a to b carbon atoms, and each selected in the range of the specified number of carbon atoms from the examples of the above-mentioned linear, branched or cyclic alkenyl group.

The aryl group means a carbocyclic aryl group or a heterocyclic aryl group.

The carbocyclic aryl group may be mentioned, for example, a phenyl group, a naphthyl group, etc.

The heterocyclic aryl group means a monocyclic or fused cyclic aryl group containing 1 to 5 hetero atoms selected from the group consisting of a nitrogen atom, an oxygen atom and a sulfur atom in the atoms constituting the ring and may be mentioned, for example, a pyridyl group, a pyrimidinyl group, a quinolyl group, a quinazolinyl group, a naphthylidinyl group, a furyl group, a pyrrolyl group, an imidazolyl group, a pyrazolyl group, an oxazolyl group, an isoxazolyl group, a triazolyl group, a thienyl group, a thiazolyl group, an isothiazolyl group, an indolyl group, a benzofuranyl group, a benzothienyl group, an imidazopyridyl group, etc.

The linear or branched aralkyl group is a linear or branched alkyl group in which any one of hydrogen atoms is substituted by a carbocyclic aryl group. There may be mentioned, for example, a benzyl group, a 1-phenylethyl group, a 2-phenylethyl group, a 4-phenylbutyl group, a 3-phenylbutyl group, a 5-phenylpentyl group, a 6-phenylhexyl group, a 8-phenyloctyl group, etc. It may be preferably mentioned a 4-phenylbutyl group, a 5-phenylpentyl group, a 6-phenylhexyl group, a 8-phenyloctyl group, etc.

In the present specification, the (Ca to Cb) linear or branched aralkyl group is the above-mentioned linear or branched aralkyl group having a to b carbon atoms, and each selected in the range of the specified number of carbon atoms from the examples of the above-mentioned linear or branched aralkyl group.

The alkoxyl group means a group in which the above-mentioned linear, branched or cyclic alkyl group is bonded to an oxy group and may be mentioned, for example, a methoxy group, an n-propoxy group, a cyclopropylmethyloxy group, an n-hexyloxy group, an isopropoxy group, an s-butoxy group, a cyclohexyloxy group, a t-butoxy group, an n-octyloxy group, etc.

In the present specification, the (Ca to Cb) alkoxyl group is the above-mentioned alkoxyl group having a to b carbon atoms, and each selected in the range of the specified number of carbon atoms from the examples of the above-mentioned alkoxyl group.

The (C2 to C12) alkenyloxy group means a group in which a linear, branched or cyclic alkenyl group having a carbon-carbon double bond at least any one of a portion thereof and having 2 to 12 carbon atoms is bonded to an oxy group and may be mentioned, for example, a 1-propenyloxy group, a 1-butenyloxy group, a 2-methyl-2-butenyloxy group, a 2-methyl-1,3-butadienyloxy group, a 1-octenyloxy group, a 1-decenyloxy group, a 1-cyclohexenyloxy group, a 3-cyclohexenyloxy group, etc.

The aralkyloxy group means a group in which the above-mentioned linear or branched aralkyl group is bonded to an oxy group, and the (C7 to C8) aralkyloxy group specifically means a group in which the above-mentioned (C7 to C8) linear or branched aralkyl group is bonded to an oxy group and may be mentioned, for example, a benzyloxy group, a phenethyloxy group, etc.

The aryloxy group means a group in which the above-mentioned aryl group is bonded to an oxy group and may be mentioned, for example, a carbocyclic aryloxy group or a heterocyclic aryloxy group, and particularly mentioned a phenoxy group, a naphthyloxy group, a pyridyloxy group, etc.

The (C1 to C6) alkylene group is a divalent substituent in which a hydrogen atom at an arbitrary position is removed from the above-mentioned (C1 to C6) linear, branched or cyclic alkyl group and may be mentioned, for example, a methylene group, an ethylene group, a propan-1,3-diyl group, a propan-1,2-diyl group, a propan-1,1-diyl group, a propan-2,2-diyl group, a 2,2-dimethyl-propan-1,3-diyl group, a hexan-1,6-diyl group, a 3-methylbutan-1,2-diyl group, a cyclopropan-1,2-diyl group, etc.

The alkylthio group means a group in which the above-mentioned linear, branched or cyclic alkyl group is bonded to a thio group, the (C1 to C8) alkylthio group specifically means a group in which the above-mentioned (C1 to C8) linear, branched or cyclic alkyl group is bonded to a thio group and may be mentioned, for example, a methylthio group, an ethylthio group, an isopropylthio group, a cyclopropylmethylthio group, a cyclopentylthio group, an n-hexylthio group, a cyclohexylthio group, etc.

The aralkylthio group means a group in which the above-mentioned linear or branched aralkyl group is bonded to a thio group, and the (C7 to C8) aralkylthio group specifically means a group in which the above-mentioned (C7 to C8) linear or branched aralkyl group is bonded to a thio group and may be mentioned, for example, a benzylthio group, a phenethylthio group, etc.

The arylthio group means a group in which the above-mentioned aryl group is bonded to a thio group and may be mentioned, for example, a carbocyclic arylthio group or a heterocyclic arylthio group, and may be particularly mentioned a phenylthio group, a naphthylthio group, a pyridylthio group, etc.

The alkylsulfinyl group means a group in which the above-mentioned linear, branched or cyclic alkyl group is bonded to a sulfinyl group, and the (C1 to C8) alkylsulfinyl group specifically means a group in which the above-mentioned (C1 to C8) linear, branched or cyclic alkyl group is bonded to a sulfinyl group and may be mentioned, for example, a methylsulfinyl group, an isopropylsulfinyl group, a cyclohexylsulfinyl group, etc.

The aralkylsulfinyl group means a group in which the above-mentioned linear or branched aralkyl group is bonded to a sulfinyl group, and the (C7 to C8) aralkylsulfinyl group specifically means a group in which the above-mentioned (C7 to C8) linear or branched aralkyl group is bonded to a sulfinyl group and may be mentioned, for example, a benzylsulfinyl group, a phenethylsulfinyl group, etc.

The arylsulfinyl group means a group in which the above-mentioned aryl group is bonded to a sulfinyl group and may be mentioned, for example, a carbocyclic arylsulfinyl group or a heterocyclic arylsulfinyl group, and may be particularly mentioned a phenylsulfinyl group, a naphthylsulfinyl group, a pyridylsulfinyl group, etc.

The alkylsulfonyl group means a group in which the above-mentioned linear, branched or cyclic alkyl group is bonded to a sulfonyl group, and the (C1 to C8) alkylsulfonyl group specifically means a group in which the above-mentioned (C1 to C8) linear, branched or cyclic alkyl group is bonded to a sulfonyl group and may be mentioned, for example, a methylsulfonyl group, an isopropylsulfonyl group, etc.

The aralkylsulfonyl group means a group in which the above-mentioned linear or branched aralkyl group is bonded to a sulfonyl group, and the (C7 to C8) aralkylsulfonyl group specifically means a group in which the above-mentioned (C7 to C8) linear or branched aralkyl group is bonded to a sulfonyl group and may be mentioned, for example, a benzylsulfonyl group, a phenethylsulfonyl group, etc.

The arylsulfonyl group means a group in which the above-mentioned aryl group is bonded to a sulfonyl group and may be mentioned, for example, a carbocyclic arylsulfonyl group or a heterocyclic arylsulfonyl group, and may be particularly mentioned a phenylsulfonyl group, a naphthylsulfonyl group, a pyridylsulfonyl group, etc.

The monoalkylamino group means a group in which the above-mentioned linear, branched or cyclic alkyl group is bonded to an amino group, and the (C1 to C10) monoalkylamino group specifically means a group in which one of the above-mentioned (C1 to C10) linear, branched or cyclic alkyl groups is bonded to an amino group. For example, there may be mentioned a methylamino group, an isopropylamino group, a neopentylamino group, an n-hexylamino group, a cyclohexylamino group, an n-octylamino group, etc.

The dialkylamino group means a group in which the same or different two of the above-mentioned linear, branched or cyclic alkyl groups are bonded to amino groups, and the (C2 to C20) dialkylamino group specifically means a group in which the same or different two of the above-mentioned (C1 to C10) linear, branched or cyclic alkyl groups are bonded to amino groups. For example, there may be mentioned a dimethylamino group, a diisopropylamino group, an N-methyl-N-cyclohexylamino group, etc.

The cyclic amino group is a group in which a hydrogen atom bonded to a nitrogen atom is removed from a 3 to 11-membered saturated heterocyclic ring containing at least one nitrogen atom as an atom constituting the ring. Specific examples may be mentioned a morpholino group, a piperazin-1-yl group, a 4-methylpiperazin-1-yl group, a piperidin-1-yl group, a pyrrolidin-1-yl group, etc.

The monoarylamino group means a group in which one of the above-mentioned aryl groups is bonded to an amino group and may be mentioned, for example, a carbocyclic arylamino group or a heterocyclic arylamino group, and may be particularly mentioned a phenylamino group, a naphthylamino group, a pyridylamino group, etc.

The diarylamino group means a group in which the same or different two of the above-mentioned aryl groups are bonded to an amino group and may be mentioned, for example, a di(carbocyclic aryl)amino group, a di(heterocyclic aryl)amino group or an N-(carbocyclic aryl)-N-(heterocyclic aryl)amino group, and particularly mentioned a diphenylamino group, an N-phenyl-N-pyridylamino group, etc.

The acyl group means a group in which a hydrogen atom, the above-mentioned linear, branched or cyclic alkyl group, the above-mentioned linear, branched or cyclic alkenyl group, an aryl group, or the above-mentioned linear or branched aralkyl group is bonded to a carbonyl group, and the (C1 to C9) acyl group specifically means a group in which a hydrogen atom, a (C1 to C8) linear, branched or cyclic alkyl group, a (C2 to C8) linear, branched or cyclic alkenyl group, an aryl group or a (C7 to C8) linear or branched aralkyl group is bonded to a carbonyl group and may be mentioned, for example, a formyl group, an acetyl group, a pivaloyl group, a benzoyl group, a pyridylcarbonyl group, etc.

The alkoxycarbonyl group means a group in which the above-mentioned alkoxyl group is bonded to a carbonyl group, and the (C2 to C9) alkoxycarbonyl group specifically means a group in which the above-mentioned (C1 to C8)

alkoxyl group is bonded to a carbonyl group and may be mentioned, for example, a methoxycarbonyl group, a t-butoxycarbonyl group, etc.

The aralkyloxycarbonyl group means a group in which the above-mentioned aralkyloxy group is bonded to a carbonyl group, and the (C8 to C9) aralkyloxycarbonyl group specifically means a group in which the above-mentioned (C7 to C8) aralkyloxy group is bonded to a carbonyl group and may be mentioned, for example, a benzyloxy-carbonyl group, etc.

The acyloxy group means a group in which the above-mentioned acyl group is bonded to an oxy group, and the (C1 to C9) acyloxy group specifically means a group in which the above-mentioned (C1 to C9) acyl group is bonded to an oxy group and may be mentioned, for example, a formyloxy group, an acetoxy group, a benzoyloxy group, a pyridylcarbonyloxy group, etc.

The alkoxycarbonyloxy group means a group in which the above-mentioned alkoxycarbonyl group is bonded to an oxy group, and the (C2 to C9) alkoxycarbonyloxy group specifically means a group in which the above-mentioned (C2 to C9) alkoxycarbonyl group is bonded to an oxy group and may be mentioned, for example, a methoxycarbonyloxy group, a t-butoxycarbonyloxy group, etc.

The aralkyloxycarbonyloxy group means a group in which the above-mentioned aralkyloxycarbonyl group is bonded to an oxy group, and the (C8 to C9) aralkyloxycarbonyloxy group specifically means a group in which the above-mentioned (C8 to C9) aralkyloxycarbonyl group is bonded to an oxy group and may be mentioned, for example, a benzyloxycarbonyloxy group, etc.

The acylamino group means a group in which the above-mentioned acyl group is bonded to an amino group, and the (C1 to C9) acylamino group specifically means a group in which the above-mentioned (C1 to C9) acyl group is bonded to an amino group and may be mentioned, for example, a formylamino group, an acetylamino group, a benzoylamino group, etc.

The alkoxycarbonylamino group means a group in which the above-mentioned alkoxycarbonyl group is bonded to an amino group, and the (C2 to C9) alkoxycarbonylamino group specifically means a group in which the above-mentioned (C2 to C9) alkoxycarbonyl group is bonded to an amino group and may be mentioned, for example, a methoxycarbonylamino group, an ethoxycarbonylamino group, etc.

The aralkyloxycarbonylamino group means a group in which the above-mentioned aralkyloxycarbonyl group is bonded to an amino group, and the (C8 to C9) aralkyloxycarbonylamino group specifically means a group in which the above-mentioned (C8 to C9) aralkyloxycarbonyl group is bonded to an amino group and may be mentioned, for example, a benzyloxycarbonylamino group, etc.

The alkylsulfonylamino group means a group in which the above-mentioned alkylsulfonyl group is bonded to an amino group, and the (C1 to C8) alkylsulfonylamino group specifically means a group in which the above-mentioned (C1 to C8) alkylsulfonyl group is bonded to an amino group and may be mentioned, for example, a methanesulfonylamino group.

The arylsulfonylamino group means a group in which the above-mentioned arylsulfonyl group is bonded to an amino group and may be mentioned, for example, a carbocyclic arylsulfonylamino group or a heterocyclic arylsulfonylamino group, and particularly mentioned a benzenesulfonylamino group, a pyridylsulfonylamino group, etc.

The carbamoyl group having a substituent(s) means a group in which the above-mentioned monoalkylamino group (for example, the above-mentioned (C1 to C10) monoalkylamino group), the above-mentioned dialkylamino group (for example, the above-mentioned (C2 to C20) dialkylamino group), the above-mentioned cyclic amino group, the above-mentioned monoarylamino group or the above-mentioned diarylamino group is bonded to a carbonyl group and may be mentioned, for example, a dimethylcarbamoyl group, a phenylcarbamoyl group, etc.

The sulfamoyl group having a substituent(s) means a group in which the above-mentioned monoalkylamino group (for example, the above-mentioned (C1 to C10) monoalkylamino group), the above-mentioned dialkylamino group (for example, the above-mentioned (C2 to C20) dialkylamino group), the above-mentioned cyclic amino group, the above-mentioned monoarylamino group or the above-mentioned diarylamino group is bonded to a sulfonyl group and may be mentioned, for example, a dimethylsulfamoyl group, a phenylsulfamoyl group, etc.

The carbamoyloxy group having a substituent(s) means a group in which the above-mentioned carbamoyl group having a substituent(s) is bonded to an oxy group and may be mentioned, for example, a dimethylcarbamoyloxy group, a phenyl-carbamoyloxy group, etc.

The sulfamoylamino group having a substituent(s) means a group in which the above-mentioned sulfamoyl group having a substituent(s) is bonded to a nitrogen atom of an amino group, the above-mentioned monoalkylamino group (for example, the above-mentioned (C1 to C10) monoalkylamino group, etc.), or the above-mentioned monoarylamino group and may be mentioned, for example, a dimethylsulfamoylamino group, etc.

The ureido group having a substituent(s) means a group in which the above-mentioned carbamoyl group having a substituent(s) is bonded to a nitrogen atom of an amino group, the above-mentioned monoalkylamino group (for example, the above-mentioned (C1 to C10) monoalkylamino group, etc.), or the above-mentioned monoarylamino group and may be mentioned, for example, a trimethylureido group, a 1-methyl-3-phenyl-ureido group, etc.

The silyl group may be mentioned a tri(C1 to C6)alkylsilyl group or a mono(C1 to C6)alkyldiarylsilyl group, for example, a trimethylsilyl group, a triethylsilyl group, a triisopropylsilyl group, a t-butyldimethylsilyl group, a t-butyldiphenylsilyl group, etc.

[With Regard to Block Copolymer]

The present invention uses a block copolymer of a polyethylene glycol segment and a hydrophobic polyester segment.

The polyethylene glycol segment in the block copolymer is a segment containing a polyethylene glycol chain which has a recurring structure of an ethyleneoxy group ($-CH_2CH_2O-$). A polymerization degree of the polyethylene glycol segment is, for example, 5 to 12,000, preferably 20 to 700, more preferably 30 to 400, further preferably 30 to 200, and particularly preferably 40 to 100. Also, an average molecular weight of the polyethylene glycol segment is, for example, 200 to 500,000, preferably 500 to 30,000, more preferably 1,000 to 10,000, further preferably 1,000 to 7,000, further more preferably 1,000 to 6,000, and particularly preferably 1,000 to 3,000. Incidentally, the average molecular weight used in the present invention is a peak top molecular weight (weight average) measured by a GPC method (Gel Permeation Chromatography) using polyethylene glycol standard products (available from Sigma Aldrich) as a standard.

One of the terminals of the polyethylene glycol segment is directly linked with a hydrophobic polyester segment mentioned later, or linked with a hydrophobic polyester segment through a boding group. Another terminal is not particularly limited, and may be a hydroxyl group of the terminal of the polyethylene glycol, or may be any terminal group obtained by modifying the terminal hydroxyl group. Accordingly, as the terminal group of another terminal, there may be mentioned a hydrogen atom, a hydroxyl group, a (C1 to C12) alkoxy group which may have a substituent(s), a (C2 to C12) alkenyloxy group which may have a substituent(s), a (C7 to C20) aralkyloxy group which may have a substituent(s), etc. As a substituent of the above-mentioned (C1 to C12) alkoxy group, the (C2 to C12) alkenyloxy group or the (C7 to C20) aralkyloxy group may be mentioned a hydroxyl group, an amino group, a formyl group, a carboxyl group, etc. It is preferably the above-mentioned (C1 to C6) alkoxyl group which may have a substituent(s), more preferably a (C1 to C6) alkoxyl group, further preferably a (C1 to C3) alkoxyl group, and further more preferably a methoxy group.

In addition, it may have a targeting molecule through the above-mentioned terminal group. The targeting molecule may be mentioned sugars, lipids, peptide and proteins and their derivatives, or folic acid, etc. Among them, for example, from the viewpoint of delivering to the liver, etc., with high specificity and efficiency, lipids and sugars are mentioned. Such lipids may be mentioned lipids such as cholesterol, fatty acids, for example, fat-soluble vitamins such as vitamin E (tocopherols, tocotrienols), vitamin A, vitamin D, vitamin K, for example, intermediate metabolites such as acylcarnitine, acyl CoA, glycolipids, glycerides, their derivatives, etc.

The sugars may be mentioned a sugar derivative having an interaction with an asialoglycoprotein receptor. The "asialoglycoprotein receptor" is present on the surface of the liver cells, and has a function of recognizing a galactose residue of the asialoglycoprotein and decomposing the same by taking the molecule thereof into the cells. The "sugar derivative having an interaction with the asialoglycoprotein receptor" is preferably a compound having a structure similar to a galactose residue and taken up into cells by interaction with the asialoglycoprotein receptor and may be mentioned, for example, GalNac (N-acetylgalactosamine) derivatives, galactose derivatives and lactose derivatives.

In addition, from the viewpoint of delivering to the brain with high specificity and efficiency, sugars (for example, glucose, sucrose, etc.) are mentioned. Also, from the viewpoint of delivering to the cancer tissues with high specificity and efficiency, folic acid and peptide (for example, cyclic peptide containing arginine-glycine-aspartic acid sequence, etc.) are mentioned. Further, from the viewpoint of delivering to each organ with high specificity and efficiency by interacting with various proteins on the surface of the cells of each organ, ligands of a receptor, antibodies, and peptide or protein of fragments thereof are mentioned.

The polyethylene glycol segment and the hydrophobic polyester segment in the block copolymer may be linked directly or indirectly through a suitable linking group, and are preferably linked directly. The bonding mode in which the polyethylene glycol segment and the hydrophobic polyester segment are directly linked is preferably an ester bond formed by a terminal hydroxyl group of the polyethylene glycol segment and a terminal carboxyl group of the hydrophobic polyester segment. The bonding group when the polyethylene glycol segment and the hydrophobic polyester segment are linked indirectly is not particularly limited as long as it is a group connecting two polymer segments by a chemical bond, and it may be a bonding group formed by a functional group capable of binding a terminal group of the polyethylene glycol segment and a terminal group of the hydrophobic polyester segment. It is preferably a (C1 to C6) alkylene group. The bonding mode of the bonding group with the polyethylene glycol segment is preferably an ether bond by a terminal oxygen atom of the polyoxyethylene) group, and the bonding mode with the hydrophobic polyester segment is preferably an amide bond or an ester bond.

The hydrophobic polyester segment in the block copolymer is a hydrophobic segment in which a monomer having a carboxyl group and a hydroxyl group in the molecule is polycondensed. It may be a homopolymer in which the monomer constituting the hydrophobic polyester segment is single, or may be a copolymer with two or more kinds. The hydrophobic polyester constituted by a single monomer may be mentioned poly(ε-caprolactone) and polylactic acid. The hydrophobic polyester constituted by two or more kinds of monomers may be mentioned poly(lactic acid-glycolic acid copolymer). In particular, poly(ε-caprolactone) is preferable.

An average molecular weight of the hydrophobic polyester segment (for example, the above-mentioned poly(ε-caprolactone), polylactic acid and poly(lactic acid-glycolic acid copolymer)) is, for example, 500 to 30,000, preferably 1,000 to 10,000, more preferably 1,000 to 8,000, further preferably 1,000 to 7,000, and further more preferably 1,000 to 3,000.

As the other embodiments, an average molecular weight of the polylactic acid is preferably 4,000 to 6,000. An average molecular weight of the poly(lactic acid-glycolic acid copolymer) is preferably 6,000 to 8,000.

As the block copolymer mentioned above, there may be mentioned a monomethoxypolyethylene glycol-poly(ε-caprolactone) copolymer, a monomethoxypolyethylene glycol-polylactic acid copolymer and a monomethoxypolyethylene glycol-poly(lactic acid-glycolic acid copolymer) copolymer, and preferred example thereof may be mentioned a monomethoxypolyethylene glycol-poly(ε-caprolactone) copolymer. Among these, a monomethoxypolyethylene glycol-poly(ε-caprolactone) copolymer in which an average molecular weight of the polyethylene glycol is 1,000 to 6,000 and an average molecular weight of the poly(ε-caprolactone) is 1,000 to 6,000 is preferable, and a monomethoxypolyethylene glycol-poly(ε-caprolactone) copolymer in which an average molecular weight of the polyethylene glycol is 1,000 to 3,000 and an average molecular weight of the poly(ε-caprolactone) is 1,000 to 3,000 is particularly preferable. Incidentally, the above-mentioned polylactic acid, and a lactic acid portion of the above-mentioned lactic acid-glycolic acid copolymer may be used either of a D-isomer, an L-isomer, or a mixture of a D-isomer and an L-isomer, and a mixture of a D-isomer and an L-isomer is preferable.

[With Regard to Manufacturing Method of Block Copolymer]

The block copolymer of the present invention can be produced by the well-known method.

For example, it can be produced by a method of bonding the polyethylene glycol segment and the hydrophobic polyester segment by an appropriate bonding mode. In addition, a block copolymer may be prepared by subjecting to a step-growth polymerization with the terminal hydroxyl group of the polyethylene glycol segment as a starting point and by a ring-opening polymerization with a cyclic ester monomer. A block copolymer is preferably prepared by subjecting to a step-growth polymerization with the terminal hydroxyl group of the polyethylene glycol segment as a starting point and a ring-opening polymerization of a cyclic ester monomer. By changing the charging ratio of the cyclic ester monomer to the polyethylene glycol segment, it is possible to obtain copolymers having various average molecular weights (polymerization degree) of each unit. By using ε-caprolactone as a cyclic ester monomer, polyethylene glycol-poly(ε-caprolactone) can be manufactured, and by using dilactide, polyethylene glycol-polylactic acid can be manufactured. By using dilactide and glycolide, polyethylene glycol-poly(lactic acid-glycolic acid copolymer) can be manufactured. Specific manufacturing method can be referred to, for example, Biomaterials, vol. 24, pp. 3563-3570 (2003), Biomaterials, vol. 26, pp. 2121-2128 (2005), International Journal of Pharmaceutics, vol. 182, pp. 187-197 (1999) and the like.

[With Regard to Peptide]

The present invention uses a peptide having 4 to 30 residues containing at least one selected from the group consisting of arginine and lysine.

The bonding mode of the peptide is a peptide bond, and may be an α conjugate or β conjugate, or may be a mixture thereof. The amino acid residue constituting the peptide may be a natural amino acid or a non-natural amino acid, and any of an L-isomer and a D-isomer can be used without any particular limitation.

The peptide preferably contains a fat-soluble group directly or through a bonding group. By containing the fat-soluble group, hydrophobic interaction with the hydrophobic polyester segment of the block copolymer increases, and stability of the composition for delivering a nucleic acid or the nucleic acid-containing composition improves.

The fat-soluble group contained in the above-mentioned peptide is not particularly limited as long as it is a fat-soluble group and selected from, for example, a (C4 to C30) linear, branched or cyclic alkyl group which may have a substituent(s), a (C4 to C30) linear, branched or cyclic alkenyl group which may have a substituent(s) and a (C7 to C30) linear or branched aralkyl group which may have a substituent(s), and preferably selected from a (C8 to C20) linear, branched or cyclic alkyl group which may have a substituent(s), a (C8 to C20) linear, branched or cyclic alkenyl group which may have a substituent(s) and a (C8 to C20) linear or branched aralkyl group which may have a substituent(s). In addition, as the other embodiments, the above-mentioned fat-soluble group is preferably selected from a group derived from cholesterol and a group derived from fat-soluble vitamin.

As a substituent(s) possessed by an alkyl group, an alkenyl group and aralkyl group in the above-mentioned fat-soluble group, there may be mentioned a sulfanyl group, a hydroxyl group, an amino group, a halogen atom, a nitro group, a cyano group, a carboxyl group, a carbamoyl group, a sulfamoyl group, a carbocyclic aryl group, a heterocyclic aryl group, an alkylthio group, an aralkylthio group, an arylthio group, an alkylsulfinyl group, an aralkylsulfinyl group, an arylsulfinyl group, an alkylsulfonyl group, an aralkylsulfonyl group, an arylsulfonyl group, a sulfamoyl group having a substituent(s), an alkoxy group, an aralkyloxy group, an aryloxy group, an acyloxy group, an alkoxycarbonyloxy group, an aralkyloxycarbonyloxy group, a carbamoyloxy group having a substituent(s), a monoalkylamino group, a dialkylamino group, a cyclic amino group, an acylamino group, an alkoxycarbonylamino group, an aralkyloxycarbonylamino group, a ureido group having a substituent(s), an alkylsulfonylamino group, an arylsulfonylamino group, a sulfamoylamino group having a substituent(s), an acyl group, an alkoxycarbonyl group, an aralkyloxycarbonyl group, a carbamoyl group having a substituent(s) and a silyl group, etc. Here, the above-mentioned carbocyclic aryl group, the heterocyclic aryl group, the alkylthio group, the arylthio group, the alkylsulfinyl group, the arylsulfinyl group, the alkylsulfonyl group, the arylsulfonyl group, the sulfamoyl group having a substituent(s), the alkoxy group, the aryloxy group, the acyloxy group, the alkoxycarbonyloxy group, the carbamoyloxy group having a substituent(s), the monoalkylamino group, the dialkylamino group, the cyclic amino group, the acylamino group, the alkoxycarbonylamino group, the ureido group having a substituent(s), the alkylsulfonylamino group, the arylsulfonylamino group, the sulfamoylamino group having a substituent(s), the acyl group, the alkoxycarbonyl group, the carbamoyl group having a substituent(s) and the silyl group, etc., may be substituted by a halogen atom, a nitro group, a cyano group, a (C1 to C8) alkoxy group, a (C7 to C8) aralkyloxy group, etc.

For example, the alkoxyl group may be mentioned a (C1 to C8) alkoxyl group.

For example, the alkoxyl group substituted by a halogen atom may be mentioned a (C1 to C8) alkoxyl group substituted by a halogen atom, and specific examples thereof are a trifluoromethoxy group, a 2,2,2-trifluoroethoxy group, etc.

For example, the alkoxycarbonyloxy group substituted by a halogen atom may be mentioned a (C2 to C9) alkoxycarbonyloxy group substituted by a halogen atom, and specific examples thereof are a trifluoromethoxycarbonyloxy group, etc.

The fat-soluble group contained in the above-mentioned peptide is more preferably a (C15 to C20) linear, branched or cyclic alkyl group, further preferably a (C15 to C20) linear or branched alkyl group, further more preferably a heptadecyl group or an octadecyl group, and particularly preferably a heptadecyl group.

The fat-soluble vitamin in the above-mentioned fat-soluble group may be mentioned vitamin A, vitamin D, vitamin E and vitamin K.

The fat-soluble group contained in the above-mentioned peptide is bonded directly or through a bonding group to the amino group at the N-terminal or the carboxyl group at the C-terminal of the peptide. When the fat-soluble group is a (C4 to C30) linear, branched or cyclic alkyl group which may have a substituent(s), a (C4 to C30) linear, branched or cyclic alkenyl group which may have a substituent(s) or a (C7 to C30) linear or branched aralkyl group which may have a substituent(s), and the above-mentioned alkyl group, alkenyl group or aralkyl group is directly bonded to the N-terminal of the peptide, the amino group at the N-terminal and the carbon atom of the above-mentioned alkyl group, the above-mentioned alkenyl group or the above-mentioned aralkyl group directly bind. However, an embodiment in which the above-mentioned alkyl group, the above-mentioned alkenyl group or the above-mentioned aralkyl group is bonded to the amino group at the N-terminal through a suitable linking group is preferable in the point of easiness in preparation.

As the suitable linking group, there may be mentioned —CO—, —O—CO—, —NH—CO—, —NH—(CH$_2$)$_\alpha$—CO—, —NH—(CH$_2$)$_\alpha$—NHCO—, —NH—(CH$_2$)$_\alpha$—OCO—, —O—(CH$_2$)$_\alpha$—CO—, —O—(CH$_2$)$_\alpha$—NHCO—, —O—(CH$_2$)$_\alpha$—OCO— and —NH—(CH$_2$)$_2$—SS—(CH$_2$)$_2$—NHCO—, etc. Here, a is an integer of 1 to 12, preferably an integer of 4 to 12, and more preferably an integer of 6 to 12.

The suitable linking group is particularly preferably —CO—.

When the fat-soluble group is a (C4 to C30) linear, branched or cyclic alkyl group which may have a substituent(s), a (C4 to C30) linear, branched or cyclic alkenyl group which may have a substituent(s) or a (C7 to C30) linear or branched aralkyl group which may have a substituent(s), and the above-mentioned alkyl group, the above-mentioned alkenyl group or the above-mentioned aralkyl group directly bonds to the C-terminal of the peptide, the above-mentioned alkyl group, the above-mentioned alkenyl group or the above-mentioned aralkyl group substitutes the hydroxyl group of the carboxyl group at the C-terminal to bond in a ketone type structure. However, an embodiment of bonding the above-mentioned alkyl group, the above-mentioned alkenyl group or the above-mentioned aralkyl group to the carboxyl group at the C-terminal through a suitable linking group is preferable in the point of easiness in preparation.

As the suitable linking group, an oxy group, an amino group or a thio group is preferable. When an oxy group (an oxygen atom) is used as the above-mentioned bonding group, the (C4 to C30) alkyl group which may have a substituent(s), the (C4 to C30) alkenyl group which may have a substituent(s) or the (C7 to C30) aralkyl group which may have a substituent(s) which is the above-mentioned fat-soluble group binds to the above-mentioned peptide in the mode of an ester bond. Also, when an amino group is used as the above-mentioned bonding group, the above-mentioned alkyl group, the above-mentioned alkenyl group or the above-mentioned aralkyl group binds to the above-mentioned peptide in the mode of an amide bond. When a thio group (a sulfur atom) is used as the above-mentioned bonding group, the above-mentioned alkyl group, the above-mentioned alkenyl group or the above-mentioned aralkyl group binds to the above-mentioned peptide in the mode of a thioester bond.

Also, as the other suitable linking groups to the carbonyl group at the C-terminal, there may be mentioned —NH—$(CH_2)_\alpha$—NH—, —O—$(CH_2)_\alpha$—NH—, —O—$(CH_2)_\alpha$—O— and —NH—$(CH_2)_2$—SS—$(CH_2)_2$—NH—, etc. Here, a is an integer of 1 to 12, preferably an integer of 4 to 12, and particularly preferably an integer of 6 to 12.

When the fat-soluble group is a group derived from cholesterol or a group derived from fat-soluble vitamin, a portion in which a hydrogen atom is removed from the hydroxyl group of the cholesterol or fat-soluble vitamin and a portion in which a hydroxyl group is removed from the carboxyl group at the C-terminal (hereinafter called as the C-terminal carbonyl group) of the above-mentioned peptide preferably bind in the mode of an ester bond. Or else, it is preferable to bind to the C-terminal carbonyl group of the above-mentioned peptide through a bonding group such as —$(CH_2)_\alpha$—NH— or —$(CH_2)_\alpha$—O—, etc. Here, a is an integer of 1 to 12, preferably an integer of 4 to 12, and particularly preferably an integer of 6 to 12.

As the other forms when the fat-soluble group is a group derived from cholesterol or a group derived from fat-soluble vitamin, a portion in which a hydrogen atom is removed from the hydroxyl group of the cholesterol or fat-soluble vitamin and the amino group at the N-terminal of the above-mentioned peptide preferably bind through a bonding group such as —CO—, —$(CH_2)_\alpha$—CO—, —$(CH_2)_\alpha$—NHCO—, —$(CH_2)_\alpha$—OCO—, —$(CH_2)_2$—SS—$(CH_2)_2$—NHCO—, etc. Here, α is an integer of 1 to 12, preferably an integer of 4 to 12, and particularly preferably an integer of 6 to 12.

A number of the residues of the peptide is 4 to 30, preferably 5 to 20, more preferably 5 to 15, further preferably 6 to 12, and particularly preferably 8 to 10.

The peptide contains at least one selected from the group consisting of arginine and lysine. Since arginine and lysine are positively charged under neutral conditions, they can form a complex with a nucleic acid having a negative charge by electrostatic interaction. Further, arginine can improve efficiency of delivering a nucleic acid by an interaction with an organelle membrane such as a cell membrane or an endosome, etc., by having a guanidine unit, so that the peptide preferably has at least one arginine.

As the other amino acid residues constituting the peptide, there may be used, for example, hydrocarbon-based amino acids such as glycine, β-alanine, alanine, leucine, isoleucine, valine, phenylalanine, etc., cyclic-based amino acids such as proline, tryptophan, etc., sulfur-based amino acids such as cysteine, etc., acidic amino acids such as aspartic acid, glutamic acid, etc., and basic amino acids such as histidine, etc. The sulfur-based amino acids such as cysteine, etc., are preferable in the point of improving stability of the composition for delivering a nucleic acid or the nucleic acid-containing composition by forming a disulfide bond between molecules. On the other hand, the basic amino acids such as histidine, etc., are preferable in the point of improving efficiency of delivering a nucleic acid by protonating under acidic biological environment to form a salt.

From the above-mentioned viewpoints, it is preferable to contain both of arginine and histidine. A total number of both residues is preferably 50 to 100% based on the total number of whole residues of the peptide, and further preferably 75 to 100%.

Preferred examples of the sequence of such a peptide may be mentioned, from the N-terminal
cysteine-histidine-histidine-arginine-arginine-arginine-arginine-histidine-histidine-cysteine (SEQ ID NO:18),
cysteine-histidine-histidine-arginine-arginine (SEQ ID NO:25), histidine-histidine-arginine-arginine-arginine-arginine-histidine-histidine (SEQ ID NO:26),
histidine-histidine-histidine-histidine-arginine-arginine-arginine-arginine (SEQ ID NO:27),
arginine-arginine-arginine-arginine-histidine-histidine-histidine-histidine (SEQ ID NO:28), etc.

A combination of the amino acid residues constituting the peptide is preferably
arginine and histidine,
arginine, histidine and cysteine,
or lysine, histidine and cysteine, and
further preferably arginine, histidine and cysteine.

[With Regard to Manufacturing Method of Peptide]

As a synthetic method of the peptides, many methods have been known. For example, a solid phase peptide synthesis has been described in "The 5$^{th}$ Edition Experimental Chemistry Course 16" edited by The Chemical Society of Japan (Maruzen, 2005, pp. 283-326), etc. The peptide of the present invention can be synthesized by, for example, using a known method described in the above-mentioned literature.

A peptide in which the fat-soluble group directly bonded to the N-terminal can be produced by reacting the terminal amino group of the peptide and a compound corresponding to the above-mentioned fat-soluble group having an aldehyde group, a ketone group, a suitable eliminatable group (a halogen, an alkylsulfonyl group, an arylsulfonyl group, etc.), an epoxy group, etc., under known N-alkylation conditions, etc.

A peptide in which the above-mentioned fat-soluble group bonded to the amino group at the N-terminal of the peptide through a bonding group can be produced by reacting the terminal amino group and a compound having a corresponding fat-soluble group, which has a carboxylic acid, an ester, an active ester (N-hydroxysuccinimidation, etc.), an acid chloride, an activated carbonic acid diester (4-nitrophenylated carbonic acid diester, etc.), an isocyanate, etc., under known N-carbonylation conditions, etc.

A peptide in which the fat-soluble group directly bonded to the C-terminal can be produced by converting the terminal carboxylic acid of the peptide to an acid chloride, an acid anhydride or an ester, and by reacting the acid chloride, the acid anhydride or the ester with an organometallic compound, etc., (for example, a Grignard reaction agent, an organic lithium compound, an organic zinc compound, etc.) having a corresponding fat-soluble group under known ketonization reactions, etc.

A peptide in which the fat-soluble group bonded to the carboxyl group at the C-terminal of the peptide through a bonding group can be produced by reacting the terminal carboxyl group of the peptide and a compound having a corresponding fat-soluble group, which has an amino group, a hydroxyl group or a thiol group by a known condensation reaction. In addition, by using a substrate in which the terminal carboxyl group of the peptide is converted into an ester, an active ester (N-hydroxysuccinimidation, etc.), an acid chloride, etc., it may be reacted by a known condensation reaction, etc.

Specific reaction conditions of the above-mentioned N-alkylation conditions, N-carbonylation conditions, ketonization reaction conditions, condensation reaction conditions can be referred to, for example, {Comprehensive Organic Transformations Second Edition, 1999, John Wiley & Sons, INC.}, etc. The peptide of the present invention can be produced by a method described in these known literatures, a method analogous thereto, or a combination thereof with a conventional method.

[With Regard to Composition for Delivering Nucleic Acid]

The composition for delivering a nucleic acid of the present invention contains a block copolymer in which a polyethylene glycol segment and a hydrophobic polyester segment are linked, and a peptide having 4 to 30 residues which contain at least one selected from the group consisting of arginine and lysine. Preferred embodiments of the above-mentioned block copolymer and the above-mentioned peptide are as described above.

As a contained ratio of the above-mentioned block copolymer and the above-mentioned peptide, the above-mentioned block copolymer is preferably 0.05 to 50 equivalents based on 1 equivalent of the above-mentioned peptide, more preferably 0.2 to 2.0 equivalents, and particularly preferably 0.5 to 1.5 equivalents.

The above-mentioned block copolymer and the above-mentioned peptide preferably form a particle, and a particle diameter thereof is preferably 100 nm or less, more preferably 50 nm or less, and particularly preferably 30 nm or less. The hydrophobic polyester segment of the block copolymer and the fat-soluble group of the above-mentioned peptide are associated by hydrophobic interaction whereby micelle particles are considered to be formed.

The above-mentioned particle diameter can be measured by a dynamic light scattering method using a light scattering particle diameter measurement device (for example, Zetasizer Nano ZS manufactured by Malvern Instruments; DLS-7000 manufactured by OTSUKA ELECTRONICS Co., LTD., etc.). The light scattering particle diameter measurement device can measure a cumulant average particle diameter or a mass average particle diameter. Either of the light scattering particle diameter measurement devices can be interchangeably used, and preferably a cumulant average particle diameter measured by Zetasizer Nano ZS manufactured by Malvern Instruments is used.

Next, a method for producing the composition for delivering a nucleic acid of the present invention will be explained.

The method for producing the composition for delivering a nucleic acid of the present invention is not particularly limited, and it is preferable to produce it by the following method in the viewpoint that a composition for delivering a nucleic acid or a nucleic acid-containing composition containing particles having a particle diameter of about 50 nm or less can be produced with high reproducibility. First, the above-mentioned block copolymer is dissolved in a water-soluble organic solvent to prepare a solution of the block copolymer. Separately, the above-mentioned peptide is dissolved in water to prepare an aqueous solution of the peptide, and this is mixed with the water-soluble organic solvent solution of the above-mentioned block copolymer. By removing the organic solvent from the mixed solution, the composition for delivering a nucleic acid is prepared in the form of an aqueous dispersion. To the solution of the prepared composition for delivering a nucleic acid, operations such as dilution, stirring, ultrasonic irradiation, dialysis and concentration, etc., may be appropriately carried out.

As the above-mentioned water-soluble organic solvent, there may be mentioned, for example, alcohol solvents such as methanol, ethanol, n-propanol, isopropyl alcohol, t-butyl alcohol, ethylene glycol, etc., ether solvents such as 1,2-dimethoxyethane, tetrahydrofuran, 1,4-dioxane, etc., ketone solvents such as acetone, etc., nitrile solvents such as acetonitrile, amide solvents such as N,N-dimethylformamide, N,N-dimethylacetamide, etc., sulfoxide solvents such as dimethylsulfoxide, etc., and the like. Preferably an ether solvent is used. Among them, it is preferable to use one or more solvents selected from tetrahydrofuran, acetone, acetonitrile, methanol, ethanol and dimethylsulfoxide, and it is more preferable to use tetrahydrofuran.

As water, water, physiological saline, an aqueous glucose solution, and a buffer solution such as a phosphate buffered physiological saline [PBS] or 4-(2-hydroxyethyl)-1-piperazineethanesulfonic acid [HEPES], etc., can be used.

As a method for removing an organic solvent from the mixed solution, there may be mentioned, for example, a method of using an ultrafiltration membrane (for example, a method of using dialysis or a centrifugal ultrafiltration device, etc.) and a solvent distillation method, etc., and a method of using an ultrafiltration membrane is preferable.

Also, a pH of the solution of each component and a mixed solution thereof can be appropriately adjusted within the range which does not impair the particle-forming ability. The pH is preferably 5 to 9, more preferably 6.5 to 8.0, and further preferably 7.0 to 8.0. Adjustment of the pH can be easily carried out by using a buffer as a solvent. A concentration of the salt of a buffer solution of the solution of each component and a mixed solution thereof can be appropriately adjusted within the range which does not impair the particle-forming ability, and is preferably 1 mM to 300 mM, more preferably 5 mM to 150 mM.

In the above-mentioned preparation method, a temperature at the time of preparing the solution of each component and a mixed solution thereof is preferably set in consideration with solubility of a polymer, and is usually 0° C. or higher, preferably 0 to 60° C., and more preferably 5 to 40° C.

In the above-mentioned preparation method, a period for equilibrating by allowing a mixed solution to stand may be provided. Specifically, for example, it is preferably allowing to stand at 0° C. to 60° C. for 0.1 to 50 hours.

In the composition for delivering a nucleic acid of the present invention, for example, generally used pharmaceutically acceptable additives may be contained to prepare nucleic acid-containing compositions with various pharmaceutical dosage forms. As the additives, there may be used, for example, excipients, extenders, fillers, binders, wetting agents, lubricants, lubricating agents, surfactants, disintegrators, solvents, solubilizers, dispersants, buffers, stabilizers, suspending agents, solubilizing aids, preservatives, antiseptics, correctives, analgesics, tonicity agents, thickening agents, pigments, flavors, etc. Such additives may be used a single kind alone, or two or more kinds in combination at an arbitrary ratio. Details of kinds and amounts to be used, etc., of these other components can be appropriately determined for those skilled in the art depending on the purpose, use, a method of use, etc., of the composition for delivering a nucleic acid or the nucleic acid-containing composition of the present invention.

As a pharmaceutical dosage form, injections and infusions, etc., are desired so that sodium chloride; salts for buffer; sugars such as glucose, lactose, mannitol, etc.; water-soluble celluloses; water-soluble polymers such as polyethylene glycol, polyvinyl alcohol, polyvinylpyrrolidone, etc.; water; water-soluble organic solvents such as glycerol, ethanol, dimethylsulfoxide, N-methylpyrrolidone, polyethylene glycol, cremophor, etc., can be further added.

The present invention includes a kit which contains the above-mentioned composition for delivering a nucleic acid, and a package insert in which a method of adding a nucleic acid to the composition for delivering a nucleic acid is integrally packaged.

The present invention includes a kit which contains a first composition containing a block copolymer in which a polyethylene glycol segment and a hydrophobic polyester segment are linked, and a second composition containing a peptide having 4 to 30 residues which contains at least one selected from the group consisting of arginine and lysine are integrally packaged. The kit may contain a package insert in which a method for preparing the above-mentioned composition for delivering a nucleic acid by mixing the above-mentioned first composition and the above-mentioned second composition is described. A contained ratio of the block copolymer and the peptide is the same as that of the composition for delivering a nucleic acid. The block copolymer and the peptide may be filled together with the above-mentioned additives and solvents.

[With Regard to Nucleic Acid-Containing Composition]

The present invention includes a nucleic acid-containing composition in which a nucleic acid is added to a composition for delivering a nucleic acid comprising the above-mentioned block copolymer and the above-mentioned peptide. The nucleic acid-containing composition can deliver the nucleic acid molecule to a target tissue and introduce it into a cell. By using the present invention, a nucleic acid having a physiological activity is delivered to a target tissue while avoiding various nucleolytic factors in a living body, the nucleic acid is introduced into a target cell, and the nucleic acid is released in the cell by escaping from an endosome whereby the function of the nucleic acid can be exerted.

In the present invention, the nucleic acid to be used is not particularly limited, and includes DNA, RNA, other natural nucleic acids, and modified nucleic acids thereof, etc. Also, as the nucleic acid, it may be a single-stranded state nucleic acid or may be a double-stranded state nucleic acid. The nucleic acid preferably has any physiological active function on a living body, a tissue, a cell, etc., after being delivered into the living body.

Examples of the nucleic acid may be mentioned plasmid DNA, siRNA, miRNA, antisense nucleic acid, shRNA, pre-miRNA, pri-miRNA, mRNA, decoy nucleic acid, ribozyme, DNA aptamer, RNA aptamer, DNA enzyme, various suppressor genes (cancer suppressor gene, etc.) and the like, and modified nucleic acid is also contained.

Examples of the modified nucleic acid may be mentioned, for example, nucleic acids in which the phosphate moiety of the nucleic acid has been modified by phosphorothioate, methylphosphonate, phosphate triester, phosphoroamidate, etc., or nucleic acids in which a hydrophobic functional group such as cholesterol and vitamin E, etc., is bonded for the purpose of stabilization of micelle particles, etc. Examples of the nucleic acid in which the sugar moiety (ribose or deoxyribose) is modified may be mentioned nucleic acids containing modified nucleotide such as hexitol nucleotide (HNA), cyclohexene nucleotide (CeNA), peptide nucleic acid (PNA), glycol nucleic acid (GNA), threonucleotide (TNA), morpholino nucleic acid, tricyclo-DNA (tcDNA), 2'-O-methylated nucleotide, 2'-O-methoxyethyl (MOE)ated nucleotide, 2'-O-amino-propyl(AP)ated nucleotide, 2'-fluorinated nucleotide, 2'-F-arabino nucleotide (2'-F-ANA), crosslinked nucleotide (BNA (Bridged Nucleic Acid)), 2'-O—(N-methylacetamid)(NMA)ated nucleotide, 2'-O-methylcarbamoylethyl(MCE)ated nucleotide, etc. Examples of the crosslinked nucleotide may be mentioned a locked nucleic acid (Locked Nucleic Acid (Registered Trademark)) also referred to as LNA, and other crosslinked nucleotides known to those skilled in the art, etc. Also, in Journal of Medicinal Chemistry, 2016, 59, pp 9645-9667, Medicinal Chemistry Communication, 2014, 5, pp 1454-1471, Future Medicinal Chemistry, 2011, 3, pp 339-365, Bioorganic & Medicinal Chemistry Letters, 2008, 18, pp. 2296-2300, WO 2007/090071, WO 2017/142054, etc., modified nucleotides are disclosed.

A kind of the nucleic acid to be used can be appropriately selected depending on the purpose and uses for obtaining a pharmacological effect by exhibiting the pharmacological activity of the nucleic acid.

For example, any plasmid DNA may be used as long as it can exert a desired function in cells of the target tissue. Various plasmids have been known as such a plasmid DNA (for example, Microbiology Spectrum, vol. 2, No. 6, 2014), and it is possible to select a desired plasmid DNA depending on the use of the composition for delivering a nucleic acid.

The siRNA and miRNA may be any material as long as it can suppress expression of the target gene by utilizing RNA interference (RNAi). Target genes for RNA interference are not particularly limited, and may be mentioned cancer (tumor) genes, anti-apoptotic genes, cell cycle-related genes, growth signal genes, transcription factor genes, etc. Also, a base length of the RNA is not limited.

In addition, the antisense nucleic acid may be a single-stranded DNA, RNA and/or a structural analogue thereof complementary to mRNA, a precursor mRNA or ncRNA (non-coding RNA; for example, ribosomal RNA, transfer RNA, miRNA, etc.) of the target gene. The target of the antisense nucleic acid is not particularly limited, and a base length of the antisense nucleic acid is also not particularly limited. Also, there may be used a double-stranded oligonucleotide containing an antisense nucleic acid and an RNA oligonucleotide complementary to the nucleic acid, and a double-stranded oligonucleotide containing an antisense nucleic acid and a PNA oligonucleotide complementary to the nucleic acid, and a double-stranded oligonucleotide containing an antisense nucleic acid and a DNA oligonucleotide complementary to the nucleic acid, etc., as described in WO 2013/089283, WO 2017/068791, WO 2017/068790 or WO 2018/003739, etc.

Also, as the antisense nucleic acid, there may be used an oligonucleotide to which an oligonucleotide containing an antisense nucleic acid and RNA complementary to the nucleic acid is linked, an oligonucleotide to which an antisense nucleic acid and PNA oligonucleotide complementary to the nucleic acid are linked, or an oligonucleotide to which an oligonucleotide containing an antisense nucleic acid and DNA complementary to the nucleic acid is linked. Link of the above-mentioned oligonucleotide may be direct or indirect through a group derived from an oligonucleotide degraded under physiological conditions or a linking group containing a non-nucleotide structure, etc. Such oligonucleotides are described in, for example, WO 2017/131124.

The "linking group containing a non-nucleotide structure" is a linking group containing at least one "non-nucleotide structure" as a constitutional unit. The non-nucleotide structure may be mentioned, for example, a structure having no nucleobase. The linking group containing a non-nucleotide structure is described in, for example, WO 2012/017919, WO 2013/103146, WO 2013/133221, WO 2015/099187, WO 2016/104775, etc., and a synthetic method of an oligonucleotide having a linking group containing a non-nucleotide structure can be also referred to these literatures.

The "oligonucleotide degraded under physiological conditions" may be an oligonucleotide degraded by enzymes such as various kinds of DNases (deoxyribo-nuclease) and RNases (ribonuclease), etc., under physiological conditions, and the nucleotides constituting the oligonucleotide may or may not be chemically modified in a part or whole of a base, a sugar or a phosphate bond. The "oligonucleotide degraded under physiological conditions" may be, for example, an oligonucleotide containing at least one phosphodiester bond, and preferably linked by a phosphodiester bond, more preferably DNA or RNA, and further preferably RNA.

The oligonucleotide degraded under physiological conditions may or may not contain a partially complementary sequence in the oligonucleotide degraded under physiological conditions, and preferably does not contain a partially complementary sequence. Examples of such oligonucleotides may be mentioned $(N)_k$ (Ns are each independently adenosine, uridine, cytidine, guanosine, 2'-deoxyadenosine, thymidine, 2'-deoxycytidine or 2'-deoxyguanosine, and k is an integer of 1 to 40 (repeating number)) linked by a phosphodiester bond. Among them, k is preferably 3 to 20, more preferably 4 to 10, further preferably 4 to 7, further more preferably 4 or 5, and particularly preferably 4.

In the present invention, the nucleic acid is, in particular, preferably RNA having a function of suppressing expression of a target gene utilizing RNA interference or an antisense nucleic acid, more preferably siRNA or miRNA, and more preferably siRNA. A base length of the siRNA is preferably 10 to 30 bases, more preferably 15 to 25 bases, further preferably 20 to 30 bases, further more preferably 20 to 25 bases, and particularly preferably 21 bases.

A base length of the antisense nucleic acid is, for example, 8 to 40 bases, preferably 10 to 30 bases, more preferably 11 to 20 bases, further preferably 12 to 14 bases, and particularly preferably 13 bases. In the case of the above-mentioned double-stranded oligonucleotide or an oligonucleotide in which an antisense nucleic acid and an RNA oligonucleotide or a PNA oligonucleotide complementary to the nucleic acid are linked, a suitable base length of the portion having a sequence of the antisense (that is, the portion having physiological activity) is the same as the base length of the above-mentioned antisense nucleic acid.

In the present invention, when a nucleic acid-containing composition is prepared by adding a nucleic acid to the above-mentioned composition for delivering a nucleic acid containing the above-mentioned block copolymer and the above-mentioned peptide, it is preferable that a complex is formed by the interaction of these constitutional components.

When the peptide has a fat-soluble group, it is preferable that micelle particles are formed by associating a nucleic acid which is an anionic charged body and a peptide which is a cationic charged body by electrostatic interaction, and further associating the hydrophobic polyester segment of the block copolymer and the fat-soluble group portion of the peptide by hydrophobic interaction.

When the peptide does not have a fat-soluble group, it is preferable that a nucleic acid which is an anionic charged body and a peptide which is a cationic charged body forms a complex by electrostatic interaction, and the complex is incorporated into inside of micelle particles which are formed by the hydrophobic polyester segments of the block copolymer by self-association due to hydrophobic interaction.

A contained ratio of the peptide and the nucleic acid of the nucleic acid-containing composition is not particularly limited as long as it is a condition in which the above-mentioned complex is formed. The above-mentioned contained ratio is preferably represented by an N/P ratio (a value obtained by dividing an N value by a P value) which is regulated by a ratio of the total number of cations (N value) of the peptide and the total number of anions (P value) of the nucleic acid.

In the nucleic acid-containing composition of the present invention, the N/P ratio is not particularly limited, and preferably 1 to 100, more preferably 1 to 50, further preferably 5 to 30, further more preferably 5 to 20, particularly preferably 5 to 15, and most preferably 10. As the other embodiments, the N/P ratio is preferably 20 to 30. By keeping the N/P ratio within the above-mentioned range, it is possible to both of improvement in stability to the nucleolytic enzymes and improvement in the intracellular introduction rate.

The preparation method of the above-mentioned nucleic acid-containing composition is not particularly limited, and it can be prepared by mixing the block copolymer, the peptide and the nucleic acid using a suitable solvent. From the viewpoint that a composition for delivering a nucleic acid or a nucleic acid-containing composition containing particles having a particle diameter of about 50 nm or less can be produced with high reproducibility, it is preferable that a composition for delivering a nucleic acid in a state of being dispersed in water is prepared by the method as mentioned above, and then, the above-mentioned nucleic acid is mixed whereby the nucleic acid-containing composition is prepared in a state of being dispersed in water. To the prepared nucleic acid-containing composition solution, appropriate operations such as dilution, stirring, ultrasonic irradiation, dialysis, concentration, etc., may be further applied.

When the peptide does not contain a fat-soluble group, an aqueous solution of the peptide and an aqueous solution of the nucleic acid are mixed, further a solution of the block copolymer in a water-soluble organic solvent is mixed, and then, the organic solvent is removed, whereby the nucleic acid-containing composition is prepared in a state of aqueous dispersion. To the solution of the prepared nucleic acid-containing composition, appropriate operations such as dilution, stirring, ultrasonic irradiation, dialysis, concentration, etc., may be further applied.

The above-mentioned water-soluble organic solvent is as described in the method of preparing the composition for delivering a nucleic acid.

As the water, in general, water, physiological saline, an aqueous glucose solution, and a buffer solution PBS and HEPES, etc., can be used.

The method of removing the organic solvent from the mixed solution, the pH of the solutions of each component and a mixed solution thereof, the temperature at the time of preparing the solutions of each component and at the time of mixing thereof, and the time of allowing the mixed solution to stand to carry out equilibration are as mentioned in the preparation method of the composition for delivering a nucleic acid above.

In the nucleic acid-containing composition of the present invention, it is preferable that the above-mentioned block copolymer, the above-mentioned peptide and the above-mentioned nucleic acid form particles, and the particle diameter is preferably 100 nm or less. By following the above-mentioned preparation method, a nucleic acid-containing composition containing particles having a particle diameter of 100 nm or less can be obtained. Further, from the viewpoint that the antitumor effect is improved due to improvement in permeability to the tumor tissue, the particle diameter of the particles of the nucleic acid-containing composition is more preferably 50 nm or less, further preferably 40 nm or less, and particularly preferably 30 nm or less. The above-mentioned particles are considered to have a micelle structure due to the hydrophobic interaction between the hydrophobic polyester segments of the block copolymer, or the hydrophobic interaction between the hydrophobic polyester segment and the fat-soluble group portion of the peptide.

The above-mentioned particle diameter can be measured by a dynamic light scattering method as in the above-mentioned composition for delivering a nucleic acid.

The nucleic acid-containing composition of the present invention may further contain a low-molecular weight drug. The nucleic acid-containing composition of the present invention containing the low-molecular weight drug can be prepared by further adding a low-molecular weight drug at the time of preparing the nucleic acid-containing composition mentioned above. The low-molecular weight drug is preferably included inside the above-mentioned particles of the nucleic acid-containing composition. The low-molecular weight drug that can be included is not particularly limited, various anticancer drugs, therapeutic agents for central nervous system diseases, various antibiotics, therapeutic agents for peripheral nerve diseases, therapeutic agents for sensory organ diseases, therapeutic agents for cardiovascular diseases, therapeutic agents for respiratory diseases, therapeutic agents for digestive system diseases, hormones agents, therapeutic agents for genitourinary tract diseases, therapeutic agents for dermatological diseases, therapeutic agents for dental and oral diseases, vitamins, nutritional tonics, cell stimulating agents and antiallergic agents, etc. Among these drugs, one kind alone may be included or two or more kinds may be included.

A preferable substance to be included is an anticancer drug. The anticancer drug that can be used is not particularly limited, and may be mentioned, for example, the following compounds: alkylating agents such as cyclophosphamide hydrate, ifosphamide, thiotepa, busulfaran, melphalan, nimustine, ranimustine, dacarpazine, temozolomide, etc.; antimetabolites such as methotrexate, pemetrexed sodium hydrate, fluorouracil, lysine doxyfluridine, capecitabine, tagafur, cytarabine, gemcitabine, fludarabine phosphate, nelarabine, cladribine, levoforinate calcium, etc.; antibiotics such as doxorubicin, daunorubicin, pirarubicin, epirubicin, idarubicin, aclarubicin, amrubicin, mitoxantrone, mitomycin C, actinomycin D, bleomycin, puperomachine, zinostatin stimalamer, calicheamicin, etc., microtubule inhibitors such as vincristine, vinblastine, vindesine, paclitaxel, docetaxel, etc.; aromatase inhibitors such as anastrozole, exemestane, letrozole, fadrozole hydrochloride hydrate, etc.; platinum preparations such as cisplatin, carboplatin, nedaplatin, oxaliplatin, etc.; topoisomerase inhibitors such as irinotecan, nogitecan, etoposide, sobuzoxane, etc.; corticosteroids such as prednisolone, dexamethasone, etc.; thalidomide derivatives such as thalidomide, lenalidomide, etc.; protease inhibitors such as bortezomib, etc. These anticancer drugs are commercially available, and one kind may be included or two or more kinds may be included.

A concentration of the above-mentioned low-molecular weight drug to be used in the preparation of the nucleic acid-containing composition can be appropriately set according to the purpose of use and may be, for example, 10 to 1,000 µM, preferably 20 to 500 µM, and more preferably 40 to 200 µM.

The nucleic acid-containing composition of the present invention can be used for a therapy (gene therapy) by delivering a desired nucleic acid to cells or tissues that cause various diseases as a target.

Diseases to be treated by the present nucleic acid-containing composition are not particularly limited, and may be mentioned cancers (for example, lung cancer, kidney cancer, brain tumor, liver cancer, breast cancer, colon cancer, neuroblastoma and bladder cancer, etc.), cardiovascular diseases, motor system disorders and central nervous system disorders, etc.

The nucleic acid-containing composition of the present invention may contain other additive commonly used for production of medicaments. Examples of the additive may be mentioned, for example, the same additive as the additive to the composition for delivering a nucleic acid, etc. Such an additive may be used one kind alone, or two or more kinds in combination at an arbitrary ratio. Details of kinds and amounts to be used and amounts, etc., of these other components can be appropriately determined for those skilled in the art depending on the purpose, use, a method of use, etc., of the pharmaceutical composition.

The nucleic acid-containing composition of the present invention can employ various preparation dosage forms, and in general, injections (among them, intravenous injections) and infusions are employed. For example, it is provided in a form of a unit dose ampule, etc. As the other forms, nasal administration, oral administration, transdermal administration, ophthalmic administration, etc., are employed.

The nucleic acid-containing composition of the present invention delivers a nucleic acid to a target cell or tissue by contacting with the target cell or tissue in vitro or in vivo. As a preferable contacting method in vitro, there may be mentioned a method in which the nucleic acid-containing composition is previously added to a medium before culture (reverse transfection method), and a method in which the nucleic acid-containing composition is added to a medium during culture afterward (forward transfection method). Also, as a preferable contacting method in vivo, there may be mentioned local administration and administration into blood, etc. By these methods, the nucleic acid can be introduced into a target cell, and the physiologically active function of the nucleic acid molecule can be efficiently exhibited.

In addition to primates such as humans, a variety of other mammalian diseases can be treated, prevented, ameliorated by the nucleic acid-containing composition of the present invention. For example, although not limited thereto, various diseases of species of mammals, including cows, sheep, goats, horses, dogs, cats, guinea pigs and other bovines, ovines, equines, canines, felines and species of rodents such as mice can be treated. In addition, the nucleic acid-containing composition of the present invention can also be treated various diseases of the other species such as birds (such as chickens).

When the nucleic acid-containing composition of the present invention is administered or fed to animals including humans, the administration dose or ingested amount thereof can be suitably selected depending on the age, body weight, symptoms or health status of the subject or the type of the composition (pharmaceuticals, food and drink) and the like, and the administration dose or ingested amount is preferably 0.0001 mg/kg/day to 100 mg/kg/day as the amount of the nucleic acid.

EXAMPLES

Next, the present invention is specifically explained by referring to Examples, but the present invention is not limited thereto.

In the following Examples, the structure of the block copolymer is represented by showing the kinds of the polyethylene glycol segment and the hydrophobic polyester segment and the molecular weight in this order. For example, the block copolymer of monomethoxypolyethylene glycol [MPEG] having a molecular weight of 2,000, and poly(ε-caprolactone) [PCL] having a molecular weight of 5,000 is abbreviated to as "MPEG-PCL (2000-5000)". The copolymer of monomethoxypolyethylene glycol and poly (lactic acid-glycolic acid) is abbreviated to as "MPEG-PLGA", and the copolymer of monomethoxypolyethylene glycol and polylactic acid is abbreviated to as "MPEG-PLA". In Examples, lactic acid portion of the poly(lactic acid-glycolic acid) portion of "MPEG-PLGA", and the polylactic acid portion of "MPEG-PLA" are a mixture of D-isomer and L-isomer.

The sequence of the peptide is indicated by the one-letter code of the IUPAC-IUB guideline in the order from N-terminal to C-terminal. For example, in the case of a peptide that is cysteine-histidine-arginine from the N-terminal is abbreviated to as "CHR". Unless otherwise particular description, amino acids are natural type. Further, when a heptadecyl group is bound to the amino group at the N-terminal of this peptide through a —CO— group, it is abbreviated to as "STR-CHR".

"FBS" means fetal bovine serum, "FBS(+)" means that the above-mentioned FBS is added, "FBS(−)" means that the above-mentioned FBS is not added, "DMEM" means Dulbecco's modified Eagle medium, "PBS" means phosphate buffered physiological saline, "HEPES" means 4-(2-hydroxyethyl)-1-piperazineethanesulfonic acid, "EDTA" means ethylenediaminetetraacetic acid, "LPS" means lipopolysaccharide, and "w/o type emulsion" means a water-in-oil type emulsion in which water droplets are dispersed in an oil phase.

In addition, in the following Examples and FIGS. 1 to 12, "Example" means Example, and "Comparative" means Comparative Example.

The block copolymer used in the following Examples can be obtained from Sigma-Aldrich, NOF Corporation, etc.

Peptides can be synthesized by conventionally known method to those skilled in the art.

siRNA can be obtained from Gene Design Co., Ltd., Nippon Gene Co., Ltd. or Cosmo Bio Inc., etc. Incidentally, in the sequence notation, "(M)" means that the base immediately before is a 2'-O-methylated nucleotide, "(L)" means that the base immediately before is a LNA (locked nucleic acid), a lower case alphabet means a deoxyribonucleotide, an upper case alphabet (excluding the alphabet attached with (M) mentioned above) means ribonucleotide, "^" means a phosphorothioate bond, and "5" means that the base of the nucleotide is 5-methylcytosine. The nucleic acids used for preparing the composition for delivering a nucleic acid are as mentioned below.

siRNA (VEGF): this is siRNA designed to target the vascular endothelial cell growth factor gene, and using 5'-CCAUGAAGCCCUGGAGUGCtt-3' (SEQ ID NO:1) as the sense strand and 5'-GCACUCCAGGGCUUCAUCGtt-3' (SEQ ID NO:2) as the antisense strand, a double strand is formed by a conventional method.

Chol-siRNA (VEGF): this is siRNA designed to target the vascular endothelial cell growth factor gene, cholesterol [Chol] is added to the 5' terminal of the sense strand, and using 5'-CCAUGAAGCCCUGGAGUGCtt-3' (SEQ ID NO:1) as the sense strand and 5'-GCACUCCAGGGCUU-CAUCGtt-3' (SEQ ID NO:2) as the antisense strand, a double strand is formed by a conventional method.

siRNA (RelA): this is siRNA designed to target the transcription factor RelA gene, and using 5'-GGUGCAGAAAGAAGACAUUtt-3' (SEQ ID NO:3) as the sense strand and 5'-AAUGUCUUCUUUCUGCACCtt-3' (SEQ ID NO:4) as the antisense strand, a double strand is formed by a conventional method.

siRNA (Plk1): this is siRNA designed to target the pol-like kinase 1 gene, and using 5'-AGAU(M)CACCCU(M)CCUU(M)AAAU(M)-3' (SEQ ID NO:5) as the sense strand and 5'-UAUUUAAG(M)GAGGGUGAU(M)CUUU-3' (SEQ ID NO:6) as the antisense strand, a double strand is formed by a conventional method.

siRNA (Cont1): this is siRNA designed for control, and using 5'-AUCCGCGCGAUAGUACGUAtt-3' (SEQ ID NO:7) as the sense strand and 5'-UACGUAC-UAUCGCGCGGAUtt-3' (SEQ ID NO:8) as the antisense strand, a double strand is formed by a conventional method.

siRNA (Cont2): this is siRNA designed for control, and using 5'-CUUACGCUGAGUACUUCGAtt-3' (SEQ ID NO:9) as the sense strand and 5'-UCGAAGUA-CUCAGCGUAAGtt-3' (SEQ ID NO:10) as the antisense strand, a double strand is formed by a conventional method.

siRNA (Luc): this is siRNA designed to target the luciferase gene, and using 5'-CUUACGCUGAGUACUUCGAtt-3' (SEQ ID NO:11) as the sense strand and 5'-UCGAAGUA-CUCAGCGUAAGtt-3' (SEQ ID NO:12) as the antisense strand, a double strand is formed by a conventional method.

FAM-siRNA (Cont1): this is siRNA designed for control, 6-carboxyfluorescein [6FAM] which is a fluorescent label is added to the 5' terminal of the antisense strand, and using 5'-AUCCGCGCGAUAGUACGUAtt-3' (SEQ ID NO:7) as the sense strand and 5'-UACGUACUAUCGCGCGGAUtt- 3' (SEQ ID NO:8) as the antisense strand, a double strand is formed by a conventional method.

Here, addition of Chol to the 5' terminal of the sense strand means that, the portion at which a hydrogen atom is removed from one hydroxyl group of Chol is bonded to the portion at which a hydrogen atom is removed from the hydroxyl group at the 5' terminal through a group represented by

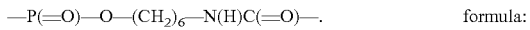

formula: —P(=O)—O—(CH$_2$)$_6$—N(H)C(=O)—.

Incidentally, in the formula, a carbon atom of the carbonyl group is bonded to the portion at which a hydrogen atom is removed from one hydroxyl group of Chol, and the phosphorus atom is bonded to the portion at which a hydrogen atom is removed from the hydroxyl group at the 5' terminal.

Also, addition of 6FAM to the 5' terminal of the antisense strand means that, the portion at which a hydroxyl group is removed from one carboxyl group of 6FAM is bonded to the portion at which a hydrogen atom is removed from the hydroxyl group at the 5' terminal through a group represented by

formula: —P(=O)—O—(CH$_2$)$_6$—N(H)—.

Incidentally, in the formula, a nitrogen atom is bonded to the portion at which a hydroxyl group is removed from one carboxyl group of 6FAM, and the phosphorus atom is bonded to the portion at which a hydrogen atom is removed from the hydroxyl group at the 5' terminal ASO (Srb1): this is an antisense nucleic acid designed to target the scavenger receptor class B member 1 gene and is 5'-T(L)^5(L)^g^t^c^a^t^g^a^c^t^T(L)^5(L)-3' (SEQ ID NO:21).

HDO (ApoB): this is a double-stranded oligonucleotide (HDO) designed to target the apolipoprotein B gene, and using 5'-G(L)^5(L)^a^t^t^g^g^t^a^t^T(L)^5(L)^A(L)-3' (SEQ ID NO:22) as the antisense strand and 5'-U(M)^G(M)^A(M)^AUACCAAU^G(M)^C(M)-3' (SEQ ID NO:23) as the sense, a double strand is formed by a conventional method.

ss-HDO (ApoB): this is a single stranded oligonucleotide designed to target the apolipoprotein B gene, which is 5'-U(M)^G(M)^A(M)^AUACCAAUGCAAAAG(L)^5(L)^a^t^t^g^g^t^a^t^T(L)^5(L)^A(L)-3' (SEQ ID NO:24), and a double strand is formed in the molecule by a conventional method.

High performance liquid chromatography (HPLC) at the time of docetaxel analysis was measured under the following conditions.
Example of HPLC Condition:
Column: XBridge BEH C18, 4.6 mm×150 mm, particle diameter 3.5 µm
Oven temperature: 35° C.
Solvent: mixed solution of acetonitrile and 0.1% aqueous sodium acetate solution
The ratio (volume ratio) of acetonitrile:0.1% aqueous sodium acetate solution was made 50:50 for 5 minutes, and 10 minutes thereafter was made 90:10.
Flow rate: 1.0 mL/min
Detection wavelength: 230 nm «Test Group A-1: Preparation 1 of Composition for Delivering Nucleic Acid»

Example 1

MPEG-PCL (2000-2000) (9.6 mg) was dissolved in tetrahydrofuran (1.0 mL), and 528 µL thereof was taken out (Solution A). A peptide (SEQ ID NO:13) (4.0 mg) having a sequence represented by STR-CHHRRRRHHC was dissolved in 50 mM HEPES buffer solution (pH=7.4, 1.6 mL), 798 µL thereof was taken out, and 100 mM dithiothreitol (750 µL) was mixed therewith (Solution B). Solution A was mixed with Solution B and after stirring the mixture, it was diluted with 10 mM HEPES buffer solution (pH=7.4, 1,650 µL), and concentrated to about 900 µL by using a centrifugal filter unit (Amicon Ultra, membrane NMWL 3,000, manufactured by Merck Millipore). Further, dilution with 10 mM HEPES buffer solution (pH=7.4, 2,400 µL) and concentration were repeated twice to obtain a composition for delivering a nucleic acid.

With regard to the particles in the composition for delivering a nucleic acid obtained above, when a cumulant average particle diameter was measured by a dynamic light scattering method using a light scattering particle diameter measurement device (Malvern Instruments, Zetasizer Nano ZS), then, it was 22 nm.

«Test Group A-2: Preparation 2 of Composition for Delivering Nucleic Acid»

Examples 2 to 8

Using the block copolymer and the peptide (SEQ ID NO:13 to 17) shown in Table 1, a composition for delivering a nucleic acid was obtained in the same manner as in Example 1. With regard to the particles in the obtained composition for delivering a nucleic acid, the results of measuring a cumulant average particle diameter by a dynamic light scattering method using a light scattering particle diameter measurement device (Malvern Instruments, Zetasizer Nano ZS) are shown in Table 1.

TABLE 1

| | Block copolymer | Peptide | Particle diameter (nm) |
|---|---|---|---|
| Example 2 | MPEG-PCL (2000-2000) | STR-HH RRRRHH (SEQ ID NO: 14) | 22 |
| Example 3 | MPEG-PCL (2000-2000) | STR-HH HHRRRR (SEQ ID NO: 15) | 21 |
| Example 4 | MPEG-PCL (2000-2000) | STR-RR RRHHHH (SEQ ID NO: 16) | 22 |
| Example 5 | MPEG-PCL (2000-2000) | STR-HR HRHRHR (SEQ ID NO: 17) | 22 |
| Example 6 | MPEG-PCL (5000-5000) | STR-CHH RRRRHHC (SEQ ID NO: 13) | 73 |
| Example 7 | MPEG-PLA (5000-5000) | STR-CHH RRRRHHC (SEQ ID NO: 13) | 69 |
| Example 8 | MPEG-PLGA (5000-7000) | STR-CHH RRRRHHC (SEQ ID NO: 13) | 57 |

«Test Group A-3: Preparation 3 of Composition for Delivering Nucleic Acid»

Example 9

MPEG-PCL (2000-2000) (9.6 mg) was dissolved in tetrahydrofuran (1.0 mL), and 528 μL thereof was taken out (Solution A). A peptide (SEQ ID NO:13) (4.0 mg) having a sequence represented by STR-CHHRRRRHHC was dissolved in 50 mM HEPES buffer solution (pH=7.4, 1.6 mL), 39.4 μL thereof was taken out, and 100 mM dithiothreitol (37.5 μL) and 10 mM HEPES buffer solution (pH=7.4, 77 μL) were mixed therewith (Solution B). Solution A was mixed with Solution B and after stirring the mixture, it was diluted with 10 mM HEPES buffer solution (pH=7.4, 165 μL), and concentrated to about 100fL by using a centrifugal filter unit (Amicon Ultra, membrane NMWL 3,000, manufactured by Merck Millipore). Further, dilution with 10 mM HEPES buffer solution (pH=7.4, 240 μL) and concentration were repeated twice to obtain a composition for delivering a nucleic acid.

With regard to the particles in the composition for delivering a nucleic acid obtained above, when a cumulant average particle diameter was measured by a dynamic light scattering method using a light scattering particle diameter measurement device (Malvern Instruments, Zetasizer Nano ZS), then, it was 21 nm.

«Test Group B-1: Preparation 1 of Nucleic Acid-Containing Composition»

Example 10 siRNA (VEGF) (150 pig) was diluted with 10 mM HEPES buffer solution (pH=7.4, 2,250 μL) (Solution C). With the composition for delivering a nucleic acid obtained in Example 1 was mixed Solution C and the mixture was stirred to obtain a nucleic acid-containing composition. In this case, the N/P ratio is 10.

With regard to the particles in the nucleic acid-containing composition obtained above, when a cumulant average particle diameter was measured by a dynamic light scattering method using a light scattering particle diameter measurement device (Malvern Instruments, Zetasizer Nano ZS), then, it was 29 nm.

«Test Group B-2: Preparation 2 of Nucleic Acid-Containing Composition»

Examples 11 to 18

The block copolymers and the peptides (SEQ ID NO:13 to 16) described in Table 2 were used and in the same method as in Example 1, compositions for delivering a nucleic acid were obtained, and then, according to the same method as in Example 10 using the compositions for delivering a nucleic acid, nucleic acid-containing compositions having an N/P ratio of 10 were obtained. With regard to the particles in the obtained nucleic acid-containing composition, cumulant average particle diameters were measured by a dynamic light scattering method using a light scattering particle diameter measurement device (Malvern Instruments, Zetasizer Nano ZS) and the results are shown in Table 2.

TABLE 2

| | Block copolymer | Peptide | N/P ratio | Particle diameter (nm) |
|---|---|---|---|---|
| Example 11 | MPEG-PCL (2000-2000) | STR-HHR RRRHH (SEQ ID NO: 14) | 10 | 30 |
| Example 12 | MPEG-PCL (2000-2000) | STR-HHH HRRRR (SEQ ID NO: 15) | 10 | 33 |
| Example 13 | MPEG-PCL (2000-2000) | STR-RRR RHHHH (SEQ ID NO: 16) | 10 | 34 |
| Example 14 | MPEG-PCL (5000-5000) | STR-HHR RRRHH (SEQ ID NO: 14) | 10 | 52 |
| Example 15 | MPEGPCL (5000 5000) | STR-CHHR RRRHHC (SEQ ID NO: 13) | 10 | 47 |
| Example 16 | MPEG-PLA (5000-5000) | STR-HHR RRRHH (SEQ ID NO: 14) | 10 | 47 |
| Example 17 | MPEG-PLGA (5000-7000) | STR-HHR RRRHH (SEQ ID NO: 14) | 10 | 64 |
| Example 18 | MPEG-PLGA (5000-7000) | STR-CHHR RRRHHC (SEQ ID NO: 13) | 10 | 73 |

«Test Group B-3: Preparation 3 of Nucleic Acid-Containing Composition»

Example 19

In the same method as in Example 10 except for using siRNA (Cont1) in place of siRNA (VEGF), a nucleic acid-containing composition having an N/P ratio of 10 was obtained.

With regard to the particles in the obtained the nucleic acid-containing composition as mentioned above, when a mass average particle diameter was measured by a dynamic light scattering method using a light scattering particle diameter measurement device (OTSUKA ELECTRONICS Co., LTD., DLS-7000), then, it was 27 nm.

«Test Group B-4: Preparation 4 of Nucleic Acid-Containing Composition»

Examples 20 to 22

In the same method as in Example 10 except for using siRNA shown in Table 3 in place of siRNA (VEGF), a nucleic acid-containing composition was obtained. With regard to the particles in the obtained compositions for delivering a nucleic acid, cumulant average particle diameters were measured by a dynamic light scattering method using a light scattering particle diameter measurement device (Malvern Instruments, Zetasizer Nano ZS) and the results are shown in Table 3.

Table 3

|  | siRNA | N/P ratio | Particle diameter (nm) |
|---|---|---|---|
| Example 20 | siRNA (Plk1) | 10 | 29 |
| Example 21 | siRNA (Cont2) | 10 | 30 |
| Example 22 | Chol-siRNA (VEGF) | 10 | 29 |

From Table 3, it could be confirmed that particles having approximately the same particle size were obtained even when the sequence of the siRNA was changed.

«Test Group B-5: Preparation 5 of Nucleic Acid-Containing Composition»

Examples 23 to 25

MPEG-PCL (2000-2000) (10 mg) was dissolved in tetrahydrofuran (1.0 mL) (Solution A1). A peptide (SEQ ID NO:13) (6.5 mg) of a sequence represented by STR-CHHRRRRHHC was dissolved in 10 mM of a HEPES buffer solution (pH=7.4, 1.0 mL) (Solution B1). siRNA (RelA) (1.0 mg) was dissolved in water (1.0 mL) (Solution C1). When Solution B1 and Solution C1 are mixed with a volume ratio of 1:1, the N/P ratio becomes 5. When these were mixed with the above-mentioned volume ratio of 2:1, 4:1 and 6:1, an N/P ratio became 10, 20 and 30, respectively.

The following shows a preparation example of the nucleic acid-containing composition when the N/P ratio is 10. Solution A1 (15.6 μL) was diluted with tetrahydrofuran (44.4 μL) to make the total amount 60 μL (Solution A2). Solution B1 (10 μL) was diluted with 10 mM HEPES buffer solution (pH=7.4, 140 μL) and the total amount was made 150 μL (Solution B2). Solution C1 (5 μL) was diluted with water (145 μL), and the total amount was made 150 μL (Solution C2).

Solution C2 was mixed with Solution B2 and after stirring the mixture for 5 seconds, Solution A2 was mixed therewith and the mixture was stirred. The mixture was concentrated using a centrifugal filter unit (Amicon Ultra, membrane NMWL3,000, manufactured by Merck Millipore). Further, dilution with water (480 μL) and concentration were repeated three times to obtain a composition for delivering a nucleic acid. This was diluted with water and the total amount was made 500 μL.

Similarly, when an N/P ratio was 20, it was prepared by using Solution A1 (31.2 μL) and Solution B1 (20 μL), and when an N/P ratio was 30, it was prepared by using Solution A1 (46.8 μL) and Solution B1 (30 μL).

With regard to the particles in the obtained nucleic acid-containing compositions, mass average particle diameters were measured by a dynamic light scattering method using a light scattering particle diameter measurement device (OTSUKA ELECTRONICS, Co., LTD., DLS-7000) and the results are shown in Table 4.

TABLE 4

|  | N/P ratio | Particle diameter (nm) |
|---|---|---|
| Example 23 | 10 | 36 |
| Example 24 | 20 | 36 |
| Example 25 | 30 | 40 |

«Test Group B-6: Preparation 6 of Nucleic Acid-Containing Composition»

Examples 26 to 27

MPEG-PCL (2000-2000) (5.0 mg) was dissolved in tetrahydrofuran (1 mL), 18 μL thereof was taken out, and diluted with tetrahydrofuran (60 μL) to make the total amount 78 μL (Solution A). The peptides (SEQ ID NO:18 to 19) (5.0 mg) having the sequence shown in Table 5 were dissolved in 10 mM HEPES buffer solution (pH=7.4, 2.0 mL), and taken out so as to be an N/P ratio of 10, and diluted with 10 mM HEPES buffer solution (pH=7.4) and the total amount was made 150 μL (Solution B). siRNA (VEGF) (50 μg) was diluted with 10 mM HEPES buffer solution (pH=7.4, 1.0 mL), then, 60 μL thereof was taken out, and further diluted with 10 mM HEPES buffer solution (pH=7.4, 90 μL) to make the total amount 150 μL (Solution C).

Solution B was mixed with Solution C and after stirring the mixture for 5 seconds, Solution A was mixed therewith and the mixture was stirred. This was diluted with 10 mM HEPES buffer solution (pH=7.4, 0.4 mL), and concentrated using a centrifugal filter unit (Amicon Ultra, membrane NMWL 3,000, manufactured by Merck Millipore). Further, dilution with 10 mM HEPES buffer solution (pH=7.4, 0.8 mL) and concentration were repeated three times to obtain a composition for delivering a nucleic acid. This was diluted with 10 mM HEPES buffer solution (pH=7.4) and made the total amount 1.0 mL.

With regard to the particles in the obtained nucleic acid-containing compositions, cumulant average particle diameters were measured by a dynamic light scattering method using a light scattering particle diameter measurement device (Malvern Instruments, Zetasizer Nano ZS) and the results are shown in Table 5.

TABLE 5

|  | Peptide sequence | N/P ratio | Particle diameter (nm) |
|---|---|---|---|
| Example 26 | CHHRRRRHHC (SEQ ID NO: 18) | 10 | 38 |
| Example 27 | GHHRRRRHH (SEQ ID NO: 19) | 10 | 42 |

«Test Group B-7: Preparation 7 of Nucleic Acid-Containing Composition»

Examples 28 to 29 siRNA (VEGF) (15 μg) was diluted with 10 mM HEPES buffer solution (pH=7.4, 225 μL) (Solution C). Also, Chol-siRNA (VEGF) (15.8 μg) was diluted with 10 mM HEPES buffer solution (pH=7.4, 225 μL) (Solution D). Solution C or Solution D was mixed with the composition for delivering a nucleic acid obtained in Example 9 and the mixture was stirred to obtain a nucleic acid-containing composition. In this case, the N/P ratio is 5.

With regard to the particles in the obtained nucleic acid-containing compositions as mentioned above, cumulant average particle diameters were measured by a dynamic light scattering method using a light scattering particle diameter measurement device (Malvern Instruments, Zetasizer Nano ZS) and the results are shown in Table 6.

TABLE 6

|  | siRNA | N/P ratio | Particle diameter (nm) |
|---|---|---|---|
| Example 28 | s I R N A (VEGF) | 5 | 30 |
| Example 29 | C h o l-s i R N A (V E G F) | 5 | 30 |

«Test Group A-4: Preparation 4 of Composition for Delivering Nucleic Acid»

Example 30

In the same method as in Example 1 except for using the peptide (SEQ ID NO:20) shown in Table 7 in place of the peptide of Example 1, a composition for delivering a nucleic acid was obtained. With regard to the particles in the obtained compositions for delivering a nucleic acid, a cumulant average particle diameter was measured by a dynamic light scattering method using a light scattering particle diameter measurement device (Malvern Instruments, Zetasizer Nano ZS) and the results are shown in Table 7.

TABLE 7

|  | Block copolymer | Peptide | Particle diameter (nm) |
|---|---|---|---|
| Example 30 | MPEG-PCL (2000-2000) | STR-CHHKKKKHHC (SEQ ID NO: 20) | 21 |

«Test Group B-8: Preparation 8 of Nucleic Acid-Containing Composition»

Example 31

In the same method as in Example 10 except for using the composition for delivering a nucleic acid obtained in Example 30 in place of that of Example 1, a nucleic acid-containing composition having an N/P ratio of 10 was obtained. With regard to the particles in the obtained nucleic acid-containing composition, when a cumulant average particle diameter was measured by a dynamic light scattering method using a light scattering particle diameter measurement device (Malvern Instruments, Zetasizer Nano ZS), then, it was 28 nm.

«Test Group B-9: Preparation 9 of Nucleic Acid-Containing Composition»

Examples 32 to 33

MPEG-PCL (2000-2000) (9.6 mg) was dissolved in tetrahydrofuran (1.0 mL), and 52.8 µL thereof was taken out (Solution A). The peptide (SEQ ID NO:13) (4.0 mg) having a sequence represented by STR-CHHRRRRHHC was dissolved in 50 mM HEPES buffer solution (pH=7.4, 1.6 mL) and 39.4 µL thereof was taken out, and it was mixed with 100 mM aqueous dithiothreitol solution (37.5 µL) and 10 mM HEPES buffer solution (pH=7.4, 77 µL) (Solution B). Docetaxel (5.0 mg) was dissolved in tetrahydrofuran (1.0 mL), and 15.0 µL or 30.0 µL thereof was taken out (Solution C). siRNA (VEGF) (150 µg) was diluted with 10 mM HEPES buffer solution (pH=7.4, 2,250 µL) (Solution D).

With Solution B were mixed Solution A and Solution C in this order, and after stirring the mixture, the mixture was diluted with 10 mM HEPES buffer solution (pH=7.4, 165 µL) and concentrated to about 100 µL using a centrifugal filter unit (Amicon Ultra, membrane NMWL 3,000, manufactured by Merck Millipore). Further, dilution with 10 mM HEPES buffer solution (pH=7.4, 240 µL) and concentration were repeated twice to obtain a docetaxel-containing composition for delivering a nucleic acid. Here, Solution C was mixed with the resulting mixture and stirred to obtain a docetaxel-containing nucleic acid-containing composition. In this case, the N/P ratio is 10.

With regard to the particles in the docetaxel-containing nucleic acid-containing composition obtained above, a cumulant average particle diameter was measured by a dynamic light scattering method using a light scattering particle diameter measurement device (Malvern Instruments, Zetasizer Nano ZS), and a contained amount and a contained ratio of docetaxel were calculated by quantitative analysis by HPLC and these results are shown in Table 8. Incidentally, the contained ratio is a value representing the contained amount with respect to the charged amount of docetaxel (the weight of docetaxel contained in Solution C) with a percentage.

TABLE 8

|  | Solution C amount | Particle diameter (nm) | Docetaxel contained amount (µg) | Docetaxel contained ratio |
|---|---|---|---|---|
| Example 32 | 15.0 µL | 29 | 32 | 43% |
| Example 33 | 30.0 µL | 29 | 65 | 43% |

«Test Group B-10: Preparation 10 of Nucleic Acid-Containing Composition»

Example 34

MPEG-PCL (2000-2000) (9.6 mg) was dissolved in tetrahydrofuran (1.0 mL), and 52.8 µL thereof was taken out (Solution A). The peptide (SEQ ID NO:13) (4.0 mg) having a sequence represented by STR-CHHRRRRHHC was dissolved in 50 mM HEPES buffer solution (pH=7.4, 1.6 mL) and 39.4 µL thereof was taken out, and it was mixed with 100 mM dithiothreitol an aqueous solution (37.5 µL) and 10 mM HEPES buffer solution (pH=7.4, 77 µL) (Solution B). Docetaxel (5.0 mg) was dissolved in tetrahydrofuran (1.0 mL), and 30.0 µL thereof was taken out (Solution C). siRNA (VEGF) (150 µg) was diluted with 10 mM HEPES buffer solution (pH=7.4, 2,250 µL) (Solution D).

With Solution B were mixed Solution A and Solution C in this order, and after stirring the mixture, the mixture was diluted with 10 mM HEPES buffer solution (pH=7.4, 165 µL) and allowed to stand under room temperature for 24 hours to spontaneously evaporate tetrahydrofuran. Thereafter, the mixture was concentrated to about 100 µL using a centrifugal filter unit (Amicon Ultra, membrane NMWL3, 000, manufactured by Merck Millipore). Further, dilution with 10 mM HEPES buffer solution (pH=7.4, 240 µL) and concentration were repeated twice to obtain a docetaxel-containing composition for delivering a nucleic acid. Here, Solution C was mixed with the resulting mixture and stirred to obtain a docetaxel-containing nucleic acid-containing composition. In this case, the N/P ratio is 10.

With regard to the particles in the docetaxel-containing nucleic acid-containing composition obtained above, a cumulant average particle diameter was measured by a dynamic light scattering method using a light scattering particle diameter measurement device (Malvern Instruments, Zetasizer Nano ZS), and a contained amount and a contained ratio of docetaxel were calculated by quantitative analysis by HPLC and these results are shown in Table 9.

TABLE 9

|  | Particle diameter (nm) | Docetaxel contained amount (μg) | Docetaxel contained ratio |
| --- | --- | --- | --- |
| Example 34 | 30 | 86 | 57% |

Comparative Example 1

With reference to the literature (international Journal of Pharmaceutics, vol. 455, pp. 40-47, 2013), a polymer obtained by conjugating MPEG-PCL (2000-2000) and the peptide (SEQ ID NO:18) having a sequence represented by CHHRRRRHHC was prepared. siRNA (Cont1) was mixed so that the N/P ratio became 10 to obtain a complex.

A mass average particle diameter of the complex obtained as mentioned above was measured by a dynamic light scattering method using a light scattering particle diameter measurement device (OTSUKA ELECTRONICS, Co., LTD., DLS-7000), and it was 88 nm.

«Test Group C: In Vitro Evaluation Cytotoxicity»

$1\times10^5$ cells of mouse macrophage cell line-like cells RAW264.7 cells were suspended in 10 mL of DMEM (containing 10% FBS, 100 U/mL penicillin and 100 μg/mL streptomycin), seeded in a flask for cell culture, and cultured at 37° C. under 5% carbon dioxide conditions. The cultured RAW264.7 cells (about 80% confluent) were washed twice with PBS, and then, detached from the flask by 0.25% trypsin-EDTA solution, and added thereto 10% FBS-containing DMEM to prepare a cell suspension with $2\times10^5$ cells/mL. This was seeded to a 96 well plate at 100 μL each and cultured for 24 hours. The medium was replaced with 90 μL of a medium (FBS(−)), and the samples prepared in Example 19 and Comparative Example 1 were each added so that siRNA (Cont1) became 100 nM per 1 well (transfection) and cultured at 37° C. under 5% carbon dioxide conditions for 4 hours. Cell viability was measured by using CellTiter-Blue (Registered Trademark) Cell Viability Assay (manufactured by Promega Corporation). Each group was carried out with n=8. An average value of the cell viability based on the control (water) is shown in FIG. 1. Incidentally, in FIG. 1, "control" means control, "Cell Viability" means cell viability, and error bars indicate standard deviation.

As shown in FIG. 1, the complex of Comparative Example 1 had a cell viability of about 60%, while the nucleic acid-containing composition of the present invention had about 80% which indicates low toxicity.

«Test Group Dain Vitro Evaluation Intracellular Uptake Efficiency»

$1\times10^5$ cells of mouse macrophage cell line-like cells RAW264.7 cells were suspended in 10 mL of DMEM (containing 10% FBS, 100 U/mL penicillin and 100 U/mL streptomycin), seeded in a flask for cell culture, and cultured at 37° C. under 5% carbon dioxide conditions. The cultured RAW264.7 cells (about 80% confluent) were washed twice with PBS, and then, detached from the flask by 0.25% trypsin-EDTA solution, and added thereto 10% FBS-containing DMEM to prepare a cell suspension with $1\times10^5$ cells/mL. This was seeded to a 24 well plate at 100 μL each and cultured for 24 hours. The medium was replaced with 900 μL of a medium of FBS(−), and in the same method as in Examples 23 to 25, each sample (N/P ratio is 10, 20 and 30) containing FAM-siRNA (Cont1) was added so that FAM-siRNA (Cont1) became 100 nM per 1 well (transfection) and cultured at 37° C. under 5% carbon dioxide conditions for 6 hours. After transfection, the cells were washed with PBS twice, 300 μL of 0.25% trypsin-EDTA solution was added thereto and the cells were cultured at 37° C. under 5% carbon dioxide conditions for 5 minutes. The cells were detached by adding 700 μL of a medium (FBS(+): the above-mentioned 10% FBS-containing DMEM), the detached cell suspension was recovered in an Eppendorf tube, and after centrifugation, the supernatant was aspirated and washed with PBS (1 mL) once and centrifuged. After removing the supernatant by suction, PBS (500 μL) was added, and the mixture was filtered through a 200-mesh nylon net to remover a cell suspension. This cell suspension was measured by Flow Cytometry (FACS Canto, Becton Dickinson) to evaluate the efficiency of uptake of the cells. On a plot showing a side scattered light to a forward scattered light, the cell population was gated, and in a plot of the cell number against the fluorescence intensity in the control of the target cell group, the range containing 95% of the cells was defined to be a P1 region, and the range where the fluorescence intensity was stronger than that was defined to be a P2 region. When FAM-siRNA (Cont1) was taken into cells, the number of cells in the P2 region increases, so that a ratio of cells contained in the P2 region of the cell population was used as an index of the amount of FAM-siRNA (Cont1) taken into the cells.

As a control, using a system in which FAM-siRNA (Cont1) alone was added at the time of transfection, and LipoTrust (Registered Trademark) EX Oligo (manufactured by Hokkaido System Science Co., Ltd.) which is a kit containing a gene or nucleic acid introducing reagent, a system according to the protocol of the kit was simultaneously carried out.

Figure 2:
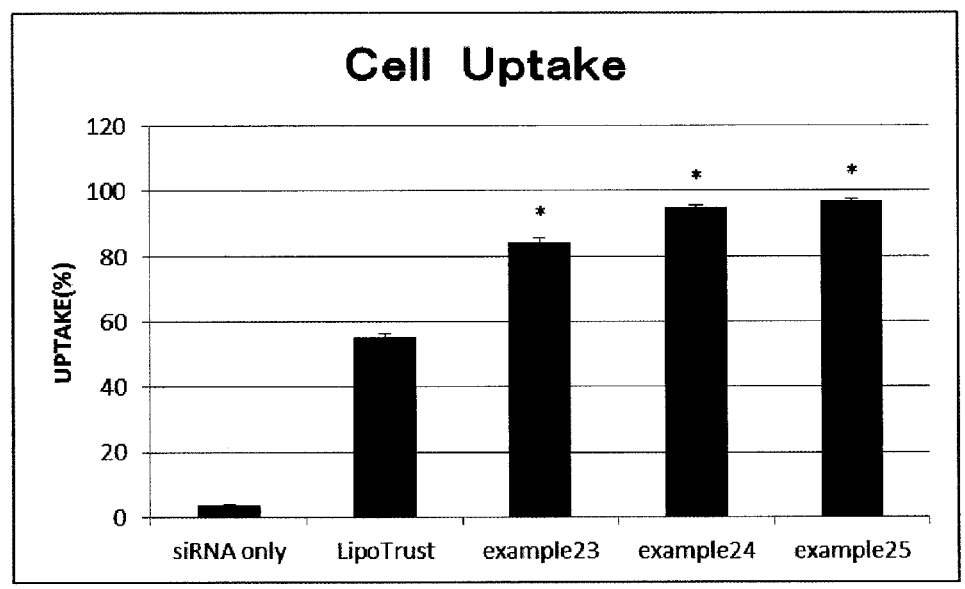
FIG. 2 is a graph showing an introducing ratio into cells of mouse macrophage cell line-like cells in the nucleic acid-containing composition according to the present embodiment.

Each group was carried out with n=8. The results are shown in FIG. 2. Incidentally, in FIG. 2, "siRNA only" means a system to which the above-mentioned FAM-siRNA (Cont1) alone was added, "LipoTrust" means a system according to the protocol of the kit using the above-mentioned LipoTrust (Registered Trademark) EX Oligo, "Cell Uptake" means a cell introducing ratio, and "Uptake" means an introducing ratio. In FIG. 2, an average value of the introducing ratio is shown and error bars indicate standard deviation. The P value (Dunnett test) compared with the LipoTrust group is indicated by the number of *, and * is P<0.001.

As shown in FIG. 2, in the nucleic acid-containing composition of the present invention, the uptake in the cells exceeded 80% in all the cases at 6 hours after transfection, and the introducing ability into the cells were confirmed to be sufficient.

«Test Group Erin Vitro Evaluation Production Inhibitory Effect of Inflammatory Cytokine Using Macrophages»

$1\times10^5$ cells of mouse macrophage cell line-like cells RAW264.7 cells were suspended in 10 mL of DMEM (containing 10% FBS, 100 U/mL penicillin and 100 U/mL streptomycin), seeded in a flask for cell culture, and cultured at 37° C. under 5% carbon dioxide conditions. The cultured RAW264.7 cells (about 80% confluent) were washed twice with PBS, and then, detached from the flask by 0.25% trypsin-EDTA solution, and added thereto 10% FBS-containing DMEM to prepare a cell suspension with $1\times10^5$ cells/mL. This was seeded to a 24 well plate at 100 μL each and cultured for 24 hours. The medium was replaced with 900 μL of a medium of FBS(−), and each sample (N/P ratio is 10, 20 or 30) prepared in the same method a in Examples 23 to 25 was added so that siRNA (RelA) became 0.5 μg per 1 well (transfection) and cultured at 37° C. under 5% carbon dioxide conditions for 6 hours. The transfected cells were washed with PBS twice, a medium (FBS(−)) was added with 1,000 μL each per 1 well and cultured at 37° C. under 5% carbon dioxide conditions for 18 hours. It was further washed with PBS twice, a medium (FBS(+): the above-mentioned 10% FBS-containing DMEM) was added with 900 μL each per 1 well, 100 μL of aqueous LPS solution (2 μg/ml) was added and cultured at 37° C. under 5% carbon dioxide conditions for 8 hours. After 8 hours from the above-mentioned LPS stimulation, the supernatant of the medium was recovered to make it as a sample. It was stored at −40° C. until at the time of use. This was used as an undiluted solution, and the production amounts of the tumor necrosis factor (TNF-α) and interleukin-6 (IL-6) were measured by Quantikine (Registered Trademark) ELISA kit (manufactured by R&D Systems). Incidentally, measurement by ELISA was carried out in accordance with the protocol of the above-mentioned kit.

As Comparative Example, a system (Control) in which without subjecting to the above-mentioned transfection and LPS stimulation, water was added in place therefor, a system (LPS only) in which without subjecting to transfection, water was added in place therefor, and a system (siRNA only) in which siRNA (RelA) only was added at the time of transfection were simultaneously carried out.

Figure 3A:
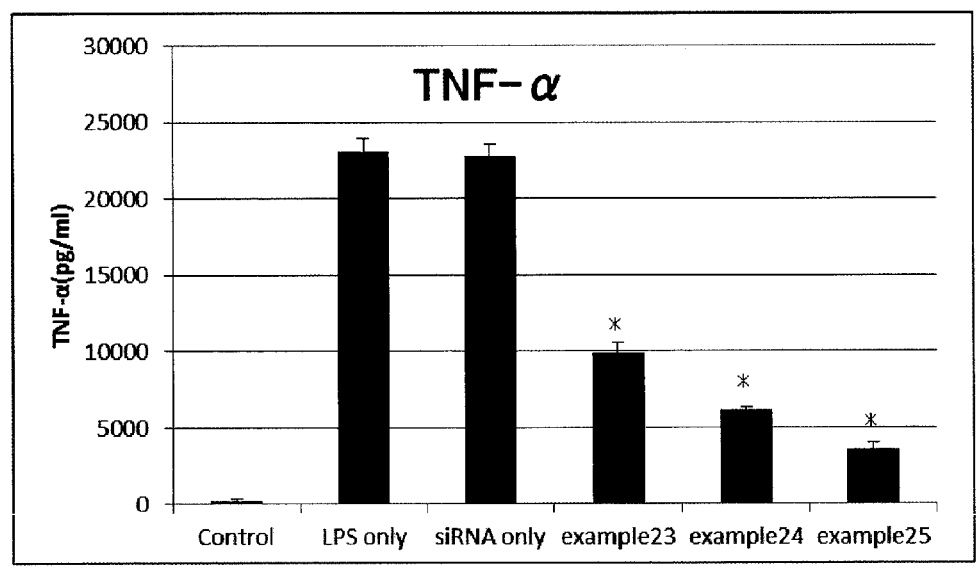
FIG. 3A is a graph showing an effect of the nucleic acid-containing composition according to the present embodiment on the amount of TNF-α produced in mouse macrophage cell line-like cells.
Figure 3B:
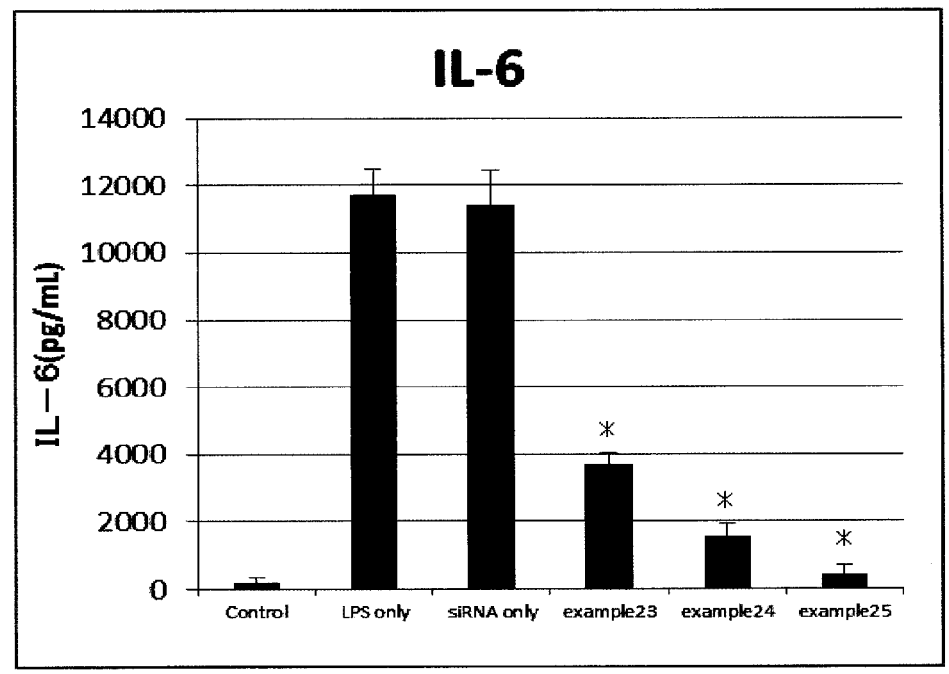
FIG. 3B is a graph showing an effect of the nucleic acid-containing composition according to the present embodiment on the amount of IL-6 produced in mouse macrophage cell line-like cells.

Each group was carried out with n=8. The production amount of TNF-α is shown in FIG. 3A, and the production amount of IL-6 is shown in FIG. 3B. Incidentally, in FIG. 3A and FIG. 3B, "control" means a system of the above-mentioned Control, "LPS only" means a system of the above-mentioned LPS only, and "siRNA only" means a system of the above-mentioned siRNA only. In FIG. 3A and FIG. 3B, average values are shown, and the error bars indicate standard deviation. The P value (Dunnett test) compared to the group of LPS only is indicated by the number of *, and * is P<0.001.

As shown in FIG. 3A and FIG. 3B, the nucleic acid-containing composition of the present invention significantly inhibited the production of inflammatory cytokines as compared with the case of LPS only and the case of siRNA only.

«Test Group F: In Vivo Evaluation Arthritis Treatment Effect of CIA Mice»

F-1: Preparation of CIA (Collagen-Induced Arthritis) Mouse

Under ice-cooling, while adding an equal amount of type II collagen solution (2 mg/mL) dropwise to complete Freund's adjuvant (CFA), the mixture was homogenized to prepare an emulsion. Similarly, while adding an equal amount of type II collagen solution (2 mg/mL) dropwise to incomplete Freund's adjuvant (IFA), the mixture was homogenized to prepare an emulsion. The prepared emulsion was confirmed to have formed a w/o type emulsion by maintaining a sphere even when it was dropped on the water surface, and was used in the experiment.

Using 8-weeks old male DBA/1J mice, CIA mice were prepared. In the following, the schedule for preparing CIA mice is shown. 100 μL of the emulsion obtained from type II collagen and CFA prepared at −21' day was intradermally administered to the tail root portion to carry out induction of the first immunization. 100 μL of the emulsion obtained from type II collagen and CFA prepared at $0^{th}$ day was similarly intradermally administered to carry out additional induction of the immunization. At this time, the intradermal administration was carried out reliably was confirmed by the fact that the administered site was protruded with white.

F-2: Administration of Nucleic Acid-Containing Composition and Pharmacological Effect The nucleic acid-containing composition (N/P ratio is 20) of siRNA (RelA) prepared in the same method as in Example 24 was administered to the tail vein of the the administration dose of siRNA (RelA) per individual became 20 μg/day, and observed until $15^{th}$ day (Each group was carried out with n=5).

As a control, a system in which physiological saline was administered to the tail vein (Non-treated CIA mice), a system in which siRNA (RelA) only was administered to the tail vein (siRNA only), and a system in which a methotrexate solution (from a solution in which 1.08 mg of methotrexate was dissolved in 75 μL of an aqueous NaOH solution (0.1 M) and 2,325 μL of physiological saline, 200 μL was used) containing 90 μg of methotrexate was intraperitoneally administered (MTX) were simultaneously carried out. Also, DBA/1J mice that did not induce collagen and did not administer any drugs were defined to be normal mice group (normal mice) (Each group was carried out with n=5).

As an index of the pharmacological effect, thickening of the hindlimb ankle joint portion and the following clinical score were used.

Thickening of the hindlimb ankle joint portion was measured by using a micrometer. After the first immunization, measurements were carried out 2-3 times a week.

Clinical score was calculated as follows.

Forelimbs: When one finger swells, 0.5 point is added. When whole forelimbs swell, 1 point is added. Therefore, the maximum clinical score in the forelimbs is to be made 3 points.

Hindlimbs: When one finger swells, 0.5 point is added. When whole hindlimbs swell, 1 point is added. For the action of walking while dragging the hindlimbs, 1 point is added. Therefore, the maximum clinical score in the hindlimbs is to be made 4.5 points.

From the above, the maximum clinical score per a mouse becomes 15 points.

Figure 4:
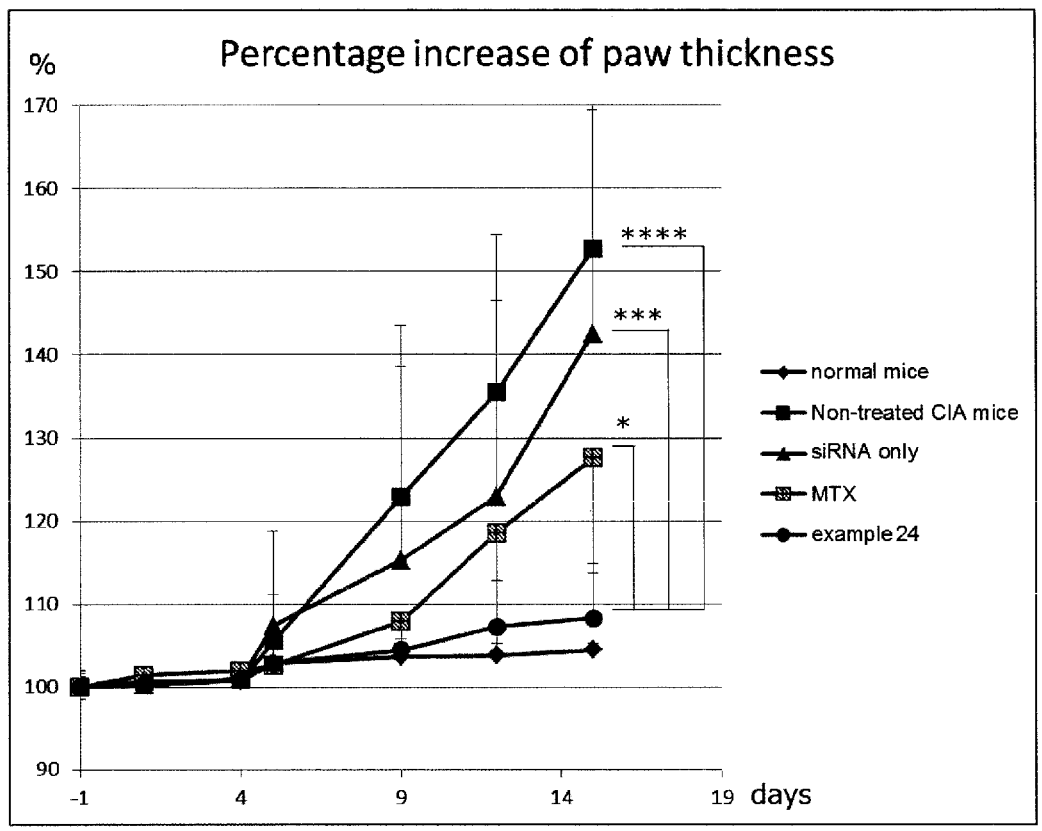
FIG. 4 is a graph showing an effect of the nucleic acid-containing composition according to the present embodiment on the thickening increasing rate of hindlimbs in CIA mice.
Figure 5:
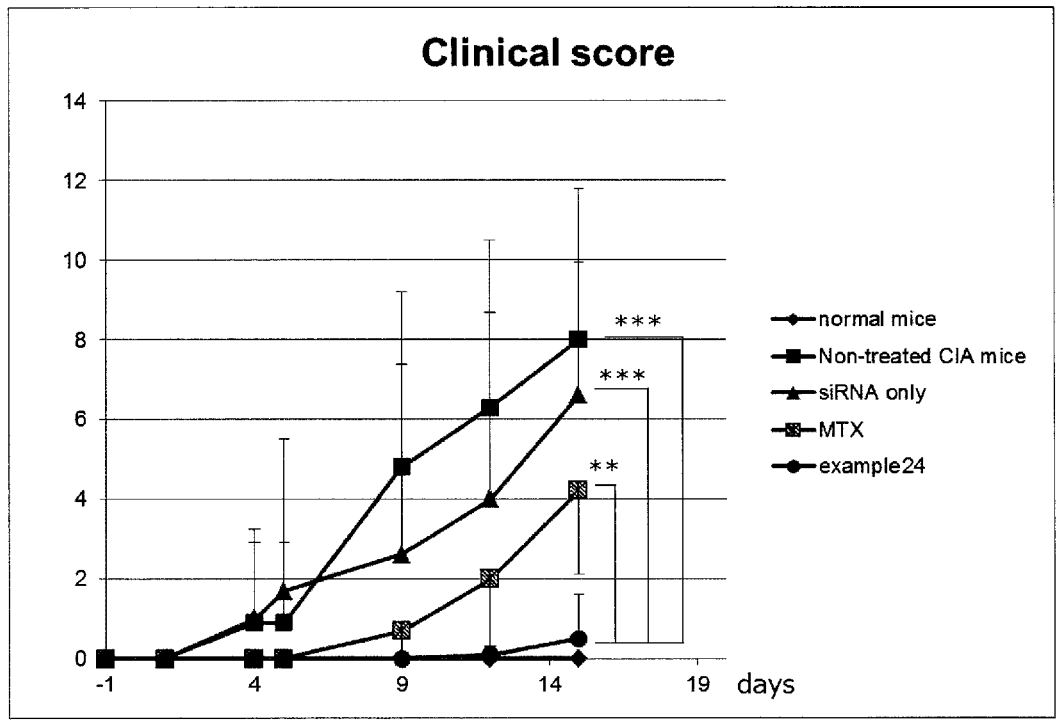
FIG. 5 is a graph showing an effect of the nucleic acid-containing composition according to the present embodiment on the clinical score in CIA mice.

The thickening increasing rate of the hindlimbs is shown in FIG. 4 and the clinical score is shown in FIG. 5. Incidentally, in FIG. 4, "percentage increase of paw thickness" means a hindlimb thickness increasing rate (%), and in FIG. 5, "Clinical score" means the clinical score. In FIG. 4 and FIG. 5, the average value is shown, and the error bars indicate standard deviation. The P value (Dunnett test) compared with the administration group of Example 24 is indicated by the number of *, * is P<0.05,  is P<0.02, * is P<0.01, and **** is P<0.002.

As shown in FIG. 4, in the untreated, siRNA only and MTX administered groups, thickening of the hindlimbs was admitted. On the other hand, in the group to which the nucleic acid-containing composition of the present invention was administered, almost no thickening was observed.

As shown in FIG. 5, in the untreated, siRNA only and MTX administered groups, remarkable increase in the clinical score was admitted. On the other hand, in the group to which the nucleic acid-containing composition of the present invention was administered, increase in the clinical score was a little.

F-3: Silencing Effect and Inflammatory Cytokine Production Inhibiting Effect of Target Molecule RelA in Four Limb Tissue On the above-mentioned $15^{th}$ day, the mice were euthanized after anesthesia, and the four limb tissues were collected. This tissue was stored at −40° C. until the time of use.

To the tissue was added 10 mL of Lysis buffer per 1 g of the tissue, shred as much as possible, and homogenized under ice-cooling. This homogenized suspension was centrifuged, and the supernatant was recovered. This supernatant was stored at −40° C. until the time of use. The above-mentioned supernatant was used as an undiluted solution, and the production amount of RelA which is the target molecule and the production amounts of the tumor necrosis factor (TNF-α) which is an inflammatory cytokine and interleukin-6 (IL-6) per 1 g of the tissue were measured by Quantikine (Registered Trademark) ELISA kit (manufactured by R&D Systems). Incidentally, measurement by ELISA was carried out in accordance with the protocol of the above-mentioned kit. Each group was carried out with n=5.

Figure 6:
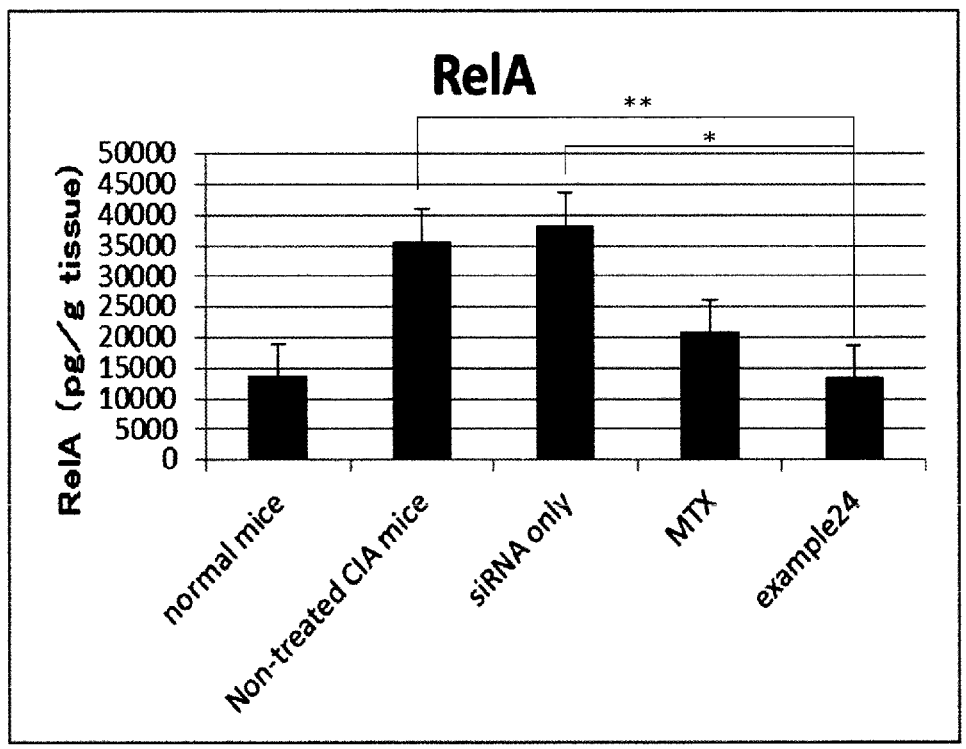
FIG. 6 is a graph showing an effect of the nucleic acid-containing composition according to the present embodiment on the production amount of RelA in the four limbs of CIA mice.
Figure 7:
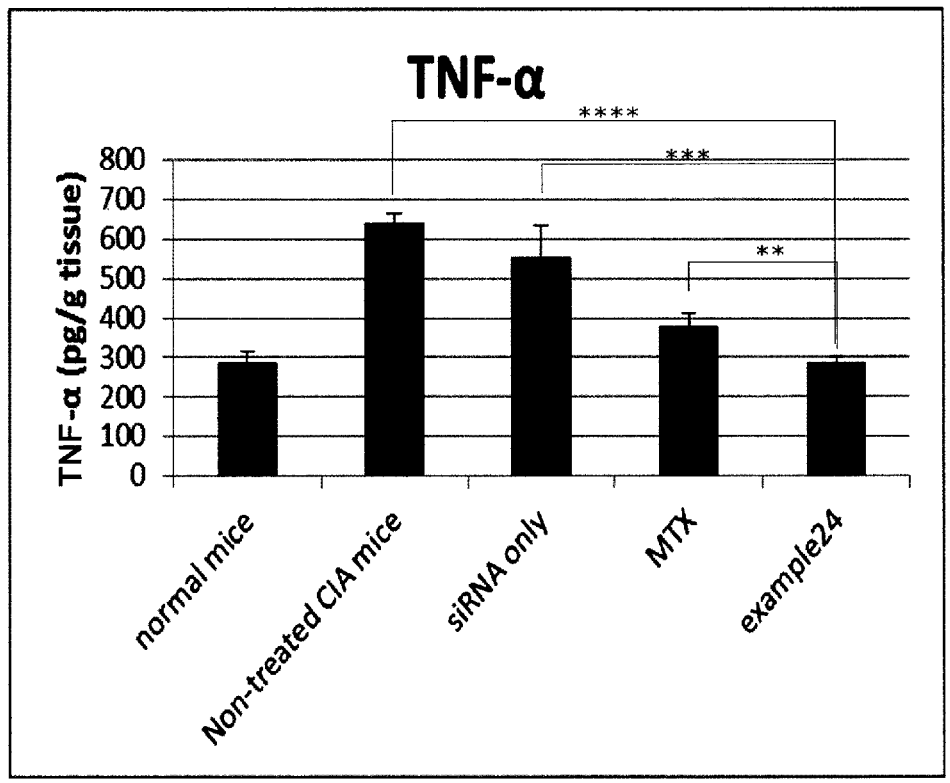
FIG. 7 is a graph showing an effect of the nucleic acid-containing composition according to the present embodiment on the production amount of TNF-α in the four limbs of CIA mice.
Figure 8:
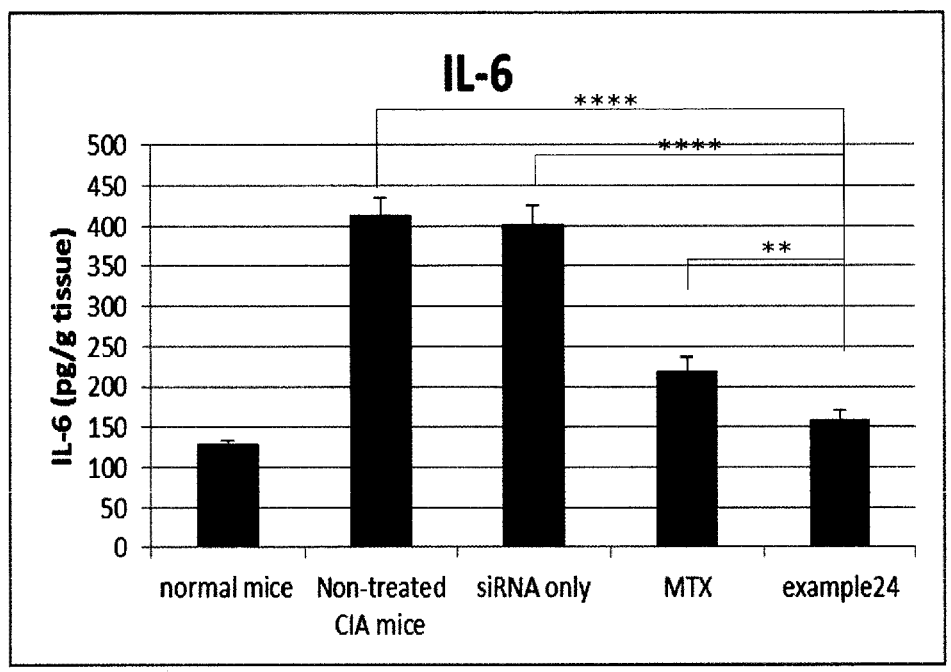
FIG. 8 is a graph showing an effect of the nucleic acid-containing composition according to the present embodiment on the production amount of IL-6 in the four limbs of CIA mice.

The production amount of RelA is shown in FIG. 6, the production amount of TNF-α is shown in FIG. 7, and the production amount of IL-6 is shown in FIG. 8. In FIG. 6 to FIG. 8, the average value is shown, the error bars indicate the standard deviation, and the P value (Dunnett test) compared with the administration group of Example 24 is indicated by the number of *. In FIG. 6, ** is P<0.01, and * is P<0.005. In FIG. 7 and FIG. 8,  is P<0.005, * is P<0.002, and **** is P<0.001.

As shown in FIG. 6, as compared with the group of untreated, siRNA only group and MTX administered group, the group to which the nucleic acid-containing composition of the present invention was administered remarkably inhibited the production of RelA. Therefore, it was suggested that the nucleic acid-containing composition of the present invention was taken up by immunocompetent cells after reaching an inflammatory site by systemic administration, and exhibited RNA interference.

As shown in FIG. 7 and FIG. 8, as compared with the group of untreated, siRNA only group and MTX administered group, in the group to which the nucleic acid-containing composition of the present invention was administered, the production amounts of TNF-α and IL-6 had significantly inhibited. In addition, in the comparison with the normal mice, the production amount was equivalent.

From these results, it was shown that productions of two inflammatory cytokines that play a central role in the pathogenesis of rheumatoid arthritis could be remarkably inhibited by administering the nucleic acid-containing composition of the present invention. Further, it was shown that the inhibiting effect was higher than methotrexate (MTX) which is an anchor drug in the current therapeutic agent for rheumatoid arthritis.

«Test Group G-1: In Vivo Evaluation Antitumor Effect of Pancreatic Cancer Cells Subcutaneously Transplanted Mice (1)»

$5\times10^6$ cells/100 µl of pancreatic cancer cells (BxPC-3) were transplanted subcutaneously to 6-week old male BALB/c-nu mice. The day when the cancer tumor mass became about 100 mm$^3$ in average ($19^{th}$ day from transplantation) was made $0^{th}$ day of treatment, and on the $0^{th}$, $3^{rd}$, $8^{th}$, $11^{th}$, $14^{th}$ and $17^{th}$ days, the sample prepared in Example 20 was administered to each mouse through the tail vein so that the administration amount of the siRNA (Plk1) became 25 µg/day per 1 mouse. Thereafter, these were observed until $29^{th}$ day (Each group was carried out with n=4).

As a control, mice (HEPES) to which a 10% HEPES buffer solution was administered through the tail vein were simultaneously observed (Each group was carried out with n=4).

Figure 9:
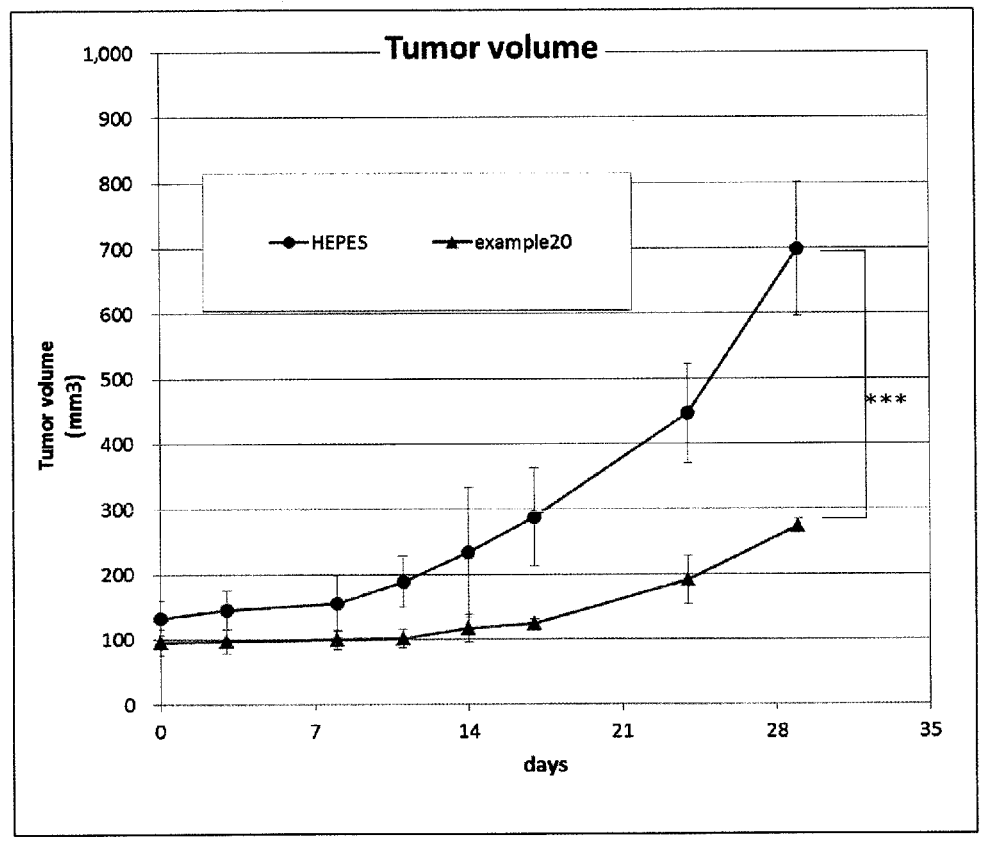
FIG. 9 is a graph showing an effect of the nucleic acid-containing composition according to the present embodiment on a tumor volume in mice subcutaneously transplanted pancreatic cancer cells.
Figure 10:
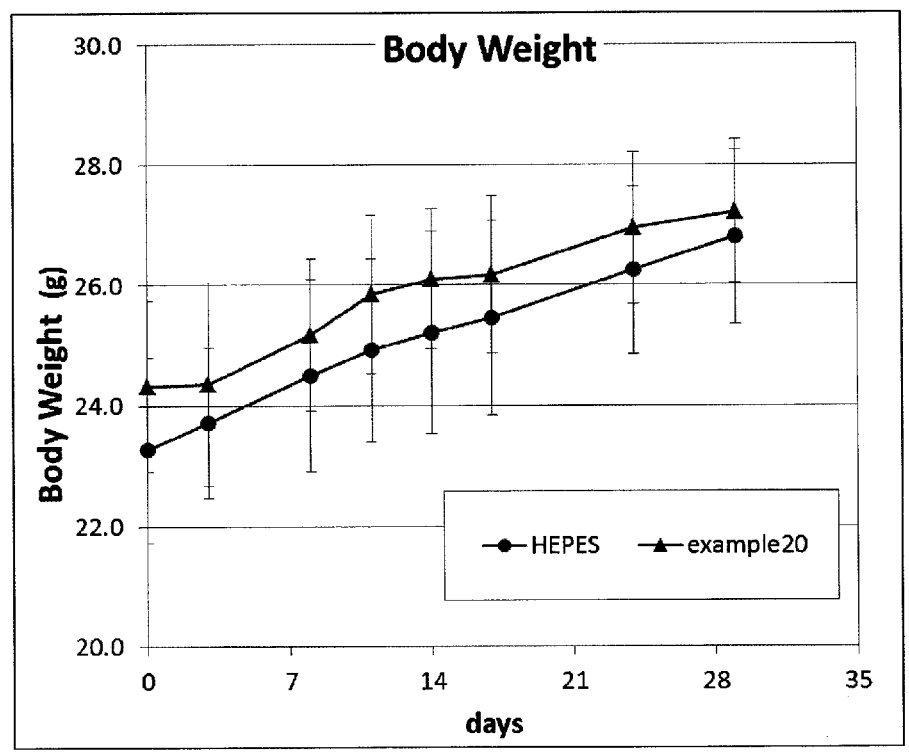
FIG. 10 is a graph showing an effect of the nucleic acid-containing composition according to the present embodiment on a body weight in mice subcutaneously transplanted pancreatic cancer cells.

Changes in tumor volume after starting administration are shown in FIG. 9, and change in body weight is shown in FIG. 10. Incidentally, in FIG. 9 and or FIG. 10, "Tumor volume" means a volume of tumor, "Body Weight" means a body weight, and "days" means a number of days. In FIG. 9 and FIG. 10, the average value is shown, and the error bars indicate standard deviation. In FIG. 10, the P value (Student test) compared with the administration group of Example 20 is indicated by the number of *, and *** is P<0.001.

As shown in FIG. 9, as compared with the group to which HEPES was administered, in the group to which the nucleic acid-containing composition of the present invention was administered, increase in the volume of tumor was significantly suppressed, and remarkable antitumor effect was confirmed. Also, as shown in FIG. 10, no difference was admitted with regard to changes in the body weight of the mice between the group to which HEPES was administered and the group to which the nucleic acid-containing composition of the present invention was administered, so that it was shown that toxicity of the nucleic acid-containing composition of the present invention is low.

«Test Group G-2: In Vivo Evaluation Antitumor Effect of Pancreatic Cancer Cells Subcutaneously Transplanted Mice (2)»

$5\times10^6$ cells/100 µl of pancreatic cancer cells (BxPC-3) were transplanted subcutaneously to 6-week old male BALB/c-nu mice. The day when the cancer tumor mass became about 100 mm$^3$ in average ($16^{th}$ day from transplantation) was made $0^{th}$ day of treatment, and on the $0^{th}$, $4^{th}$, $10^{th}$, $13^{rd}$, $17^{th}$, $20^{th}$, $24^{th}$ and $28^{th}$ days, the sample prepared in Example 20 was administered to each mouse through the tail vein so that the administration amount of the siRNA (Plk1) became 25 µg/day per 1 mouse. Thereafter, these were observed until $38^{th}$ day (Each group was carried out with n=5).

As a control, mice (HEPES) to which a 10% HEPES buffer solution was administered through the tail vein were simultaneously carried out (N=4). Further, as a control, using siRNA (Luc) in place of siRNA (Plk1), mice (siRNA (Luc)) to which a sample prepared by the method described in Example 20 was administered through the tail vein were simultaneously observed (Each group was carried out with n=5).

Also, on the $38^{th}$ day, with regard to the siRNA (Plk1) administered group and the HEPES administered group, blood biochemical tests were carried out according to a standard method.

Figure 11:
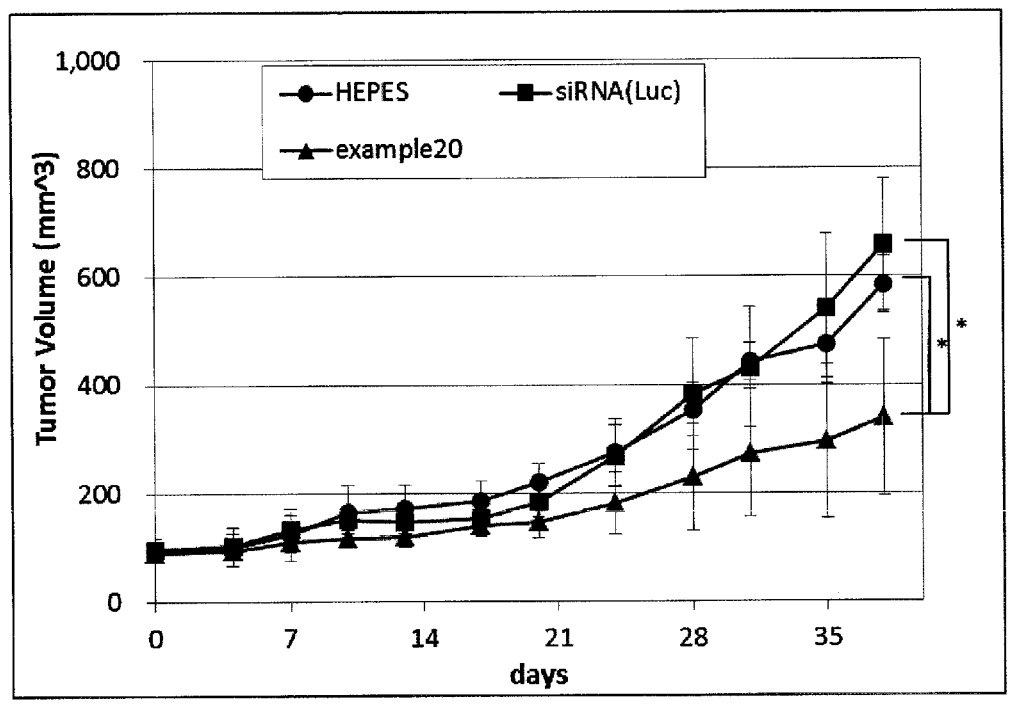
FIG. 11 is a graph showing an effect of the nucleic acid-containing composition according to the present embodiment on a tumor volume in mice subcutaneously transplanted pancreatic cancer cells.
Figure 12:
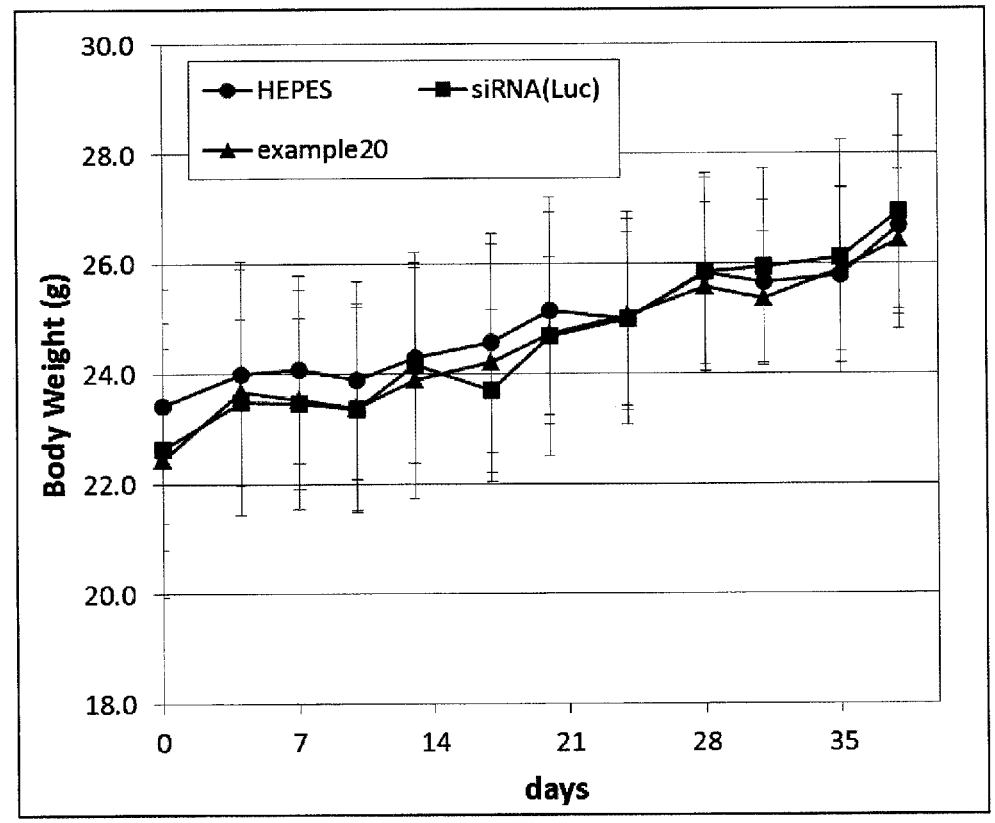
FIG. 12 is a graph showing an effect of the nucleic acid-containing composition according to the present embodiment on a body weight in mice subcutaneously transplanted pancreatic cancer cells.

Changes in the volume of tumor after starting administration are shown in FIG. 11, changes in a body weight are shown in FIG. 12, and the results of blood biochemical tests are shown in Table 10. Incidentally, in FIG. 11 and FIG. 12 "Tumor volume" means a volume of tumor, "Body Weight" means a body weight, and "days" means a number of days. In FIG. 11 and FIG. 12, the average value is shown, and the error bars indicate standard deviation. The P value (Wilcoxon test) compared with the administration group of Example 20 is indicated by the number of *, and * is P<0.001. Each item in Table 10 is shown as an average value±standard deviation.

TABLE 10

|  | HEPES | siRNA (Plk1) |
|---|---|---|
| GOT (U/l) | 46 ± 7.2 | 50 ± 2.5 |
| GPT (U/l) | 24 ± 2.5 | 27 ± 1.5 |
| ALP (U/l) | 277 ± 33.1 | 277 ± 23.1 |
| GGT (U/l) | 1 ± 0.0 | 1 ± 0.0 |
| ALB (g/dl) | 2.0 ± 0.12 | 2.0 ± 0.15 |
| BUN (mg/dl) | 20.9 ± 1.27 | 22.2 ± 1.42 |
| CRE (mg/dl) | 0.2 ± 0.06 | 0.2 ± 0.12 |

As shown in FIG. 11, as compared with the group to which HEPES or siRNA (Luc) was administered, in the group to which the nucleic acid-containing composition of the present invention was administered, increase in the volume of tumor was significantly suppressed, and remarkable antitumor effect was confirmed. Also, in the group to which HEPES was administered and the group to which siRNA (Luc) was administered, no difference in the antitumor effect was observed, so that the present antitumor effect was suggested to be derived from knockdown of Plk1. As shown in FIG. 12 and Table 10, no difference was admitted with regard to changes in the body weight of the mice and each parameter in the blood biochemical test between each group, so that it was shown that toxicity of the nucleic acid-containing composition of the present invention is low.

«Test Group H a In Vitro Evaluation Spheroid Permeability»

$1 \times 10^5$ cells of adenocarcinomic human alveolar basal epithelial cells of A549 cell were suspended in 10 mL of DMEM (containing 10% FBS, 100 U/mL penicillin and 100 U/mL streptomycin), seeded in a flask for cell culture, and cultured at 37° C. under 5% carbon dioxide conditions. The cultured A549 cells (about 80% confluent) were washed with PBS twice, detached from the flask by 0.25% trypsin-EDTA solution, and added thereto 10% FBS-containing DMEM to make a cell suspension with $1 \times 10^5$ cells/mL. This was seeded at $2.0 \times 10^4$ cells/well to 96 well plate for spheroid (PrimeSurface™ MS-9096U 96well plate, Sumitomo Bakelite), and cultured for 4 days to prepare A549 aggregates (spheroids). 50 µL of the medium of the A549 spheroids in the cultured each well was removed, and in the same method as in Example 23 and 25, each sample (N/P ratio is 10 or 30) containing FAM-siRNA (Cont1) was added so that FAM-siRNA (Cont1) became 200 nM per 1 well (transfection) and cultured at 37° C. under the conditions of 5% carbon dioxide for 10 hours. The solution was removed, 4% paraformaldehyde-phosphate buffer solution was added at 100 µL/well and the mixture was reacted for 10 minutes to fix spheroids. After washing with PBS twice and replacing with 200 µL of water, a cross section at a position of 200 µm from the spheroid surface was photographed with a confocal laser microscope (FV1000DIX81, Olympus).

As a control, at the time of transfection, a system to which FAM-siRNA (Cont1) alone was added, and a system to which a complex in which FAM-siRNA (Cont1) and the peptide having a sequence represented by STR-CHHRRR-RHHC were mixed with an N/P ratio of 10 or 30 was added were simultaneously carried out.

Figure 13:
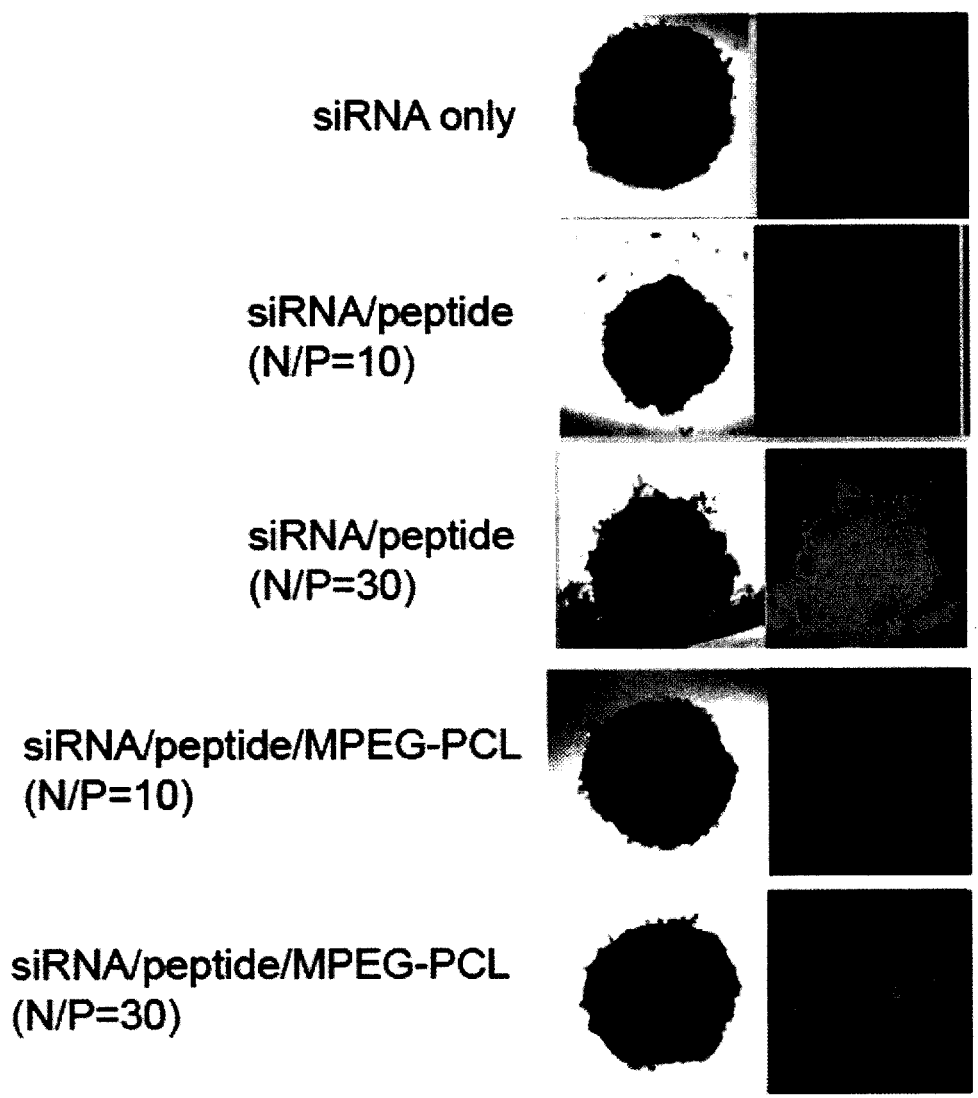
FIG. 13 is a confocal laser micrograph showing spheroid permeability of the nucleic acid-containing composition according to the present embodiment in adenocarcinomic human alveolar basal epithelial cells.

The results are shown in FIG. 13. Incidentally, in FIG. 13, "siRNA only" means a system to which the above-mentioned FAM-siRNA (Cont1) alone was added, "siRNA+peptide" means a system to which a complex in which FAM-siRNA (Cont1) and the peptide having a sequence represented by STR-CHHRRRRHHC were mixed was added, and "siRNA+peptide+MPEG-PCL" means a system to which the nucleic acid-containing composition of the present invention (a complex (similar to Example 23 or 25) in which the above-mentioned FAM-siRNA (Cont1), the peptide having a sequence represented by STR-CHHRRR-RHHC and MPEG-PCL (2000-2000) were mixed) was added.

As shown in FIG. 13, it was shown that permeability to spheroids was low in siRNA only and the complex (N/P ratio is 10) of the siRNA and the peptide. Also, in the complex (N/P ratio is 30) of the siRNA and the peptide, destruction of spheroid was observed and high cytotoxicity was suggested. On the other hand, the nucleic acid-containing composition of the present invention showed high permeability to spheroids in either of the N/P ratios, and there was no spheroid destruction.

«Test Group B-10: Preparation 10 of Nucleic Acid-Containing Composition»

Examples 35 to 37

A nucleic acid-containing composition was obtained in the same method as in Example 10 using the nucleic acid described in Table 11 in place of siRNA (VEGF). With regard to the particles in the obtained nucleic acid-containing compositions, cumulant average particle diameters were measured by a dynamic light scattering method using a light scattering particle diameter measurement device (Malvern Instruments, Zetasizer Nano ZS) and the results are shown in Table 11.

TABLE 11

| | Nucleic acid | N/P ratio | Particle diameter (nm) |
|---|---|---|---|
| Example 35 | ASO (Srb1) | 10 | 28 |
| Example 36 | HDO (ApoB) | 10 | 30 |
| Example 37 | ss-HDO (ApoB) | 10 | 31 |

«Test Group H-2: In Vitro Evaluation Spheroid Permeability 2»

$1 \times 10^5$ cells of mouse breast cancer cells of 4T1 cells were suspended in 10 mL of RPMI1640 medium (containing 10% FBS, 1% penicillin and 1% streptomycin), seeded in a flask for cell culture, and cultured at 37° C. under 5% carbon dioxide conditions. The cultured 4T1 cells (about 80% confluent) were washed with PBS twice, detached from the flask by 0.25% trypsin-EDTA solution, and 10% FBS-containing RPMI1640 was added to make a cell suspension with $1 \times 10^5$ cells/mL. This was seeded to 96 well plate for spheroid (PrimeSurface™ MS-9096U 96 well plate, Sumitomo Bakelite) with $1.0 \times 10^4$ cells/100 µL/well and cultured for 3 days to prepare 4T1 aggregates (spheroids). 50 µL of the medium of the 4T1 spheroids in the cultured each well was removed, and in the same method as in Example 10, each sample (N/P ratio is 10) containing FAM-siRNA (Cont1) was added so that FAM-siRNA (Cont1) became 100 nM per 1 well (transfection) and cultured at 37° C. under 5% carbon dioxide conditions for 6 hours. The solution was removed, 4% paraformaldehyde-phosphate buffer solution was added at 90 µL/well and the mixture was reacted for 30 minutes to fix spheroids. After washing with PBS twice and replacing with 200 µL, of water, a cross section at a position of 80 µm from the spheroid surface was photographed with a confocal laser microscope (FV1000DIX81, Olympus).

As a control, a system to which FAM-siRNA (Cont1) alone was added at the time of transfection was simultaneously carried out.

Figure 14:
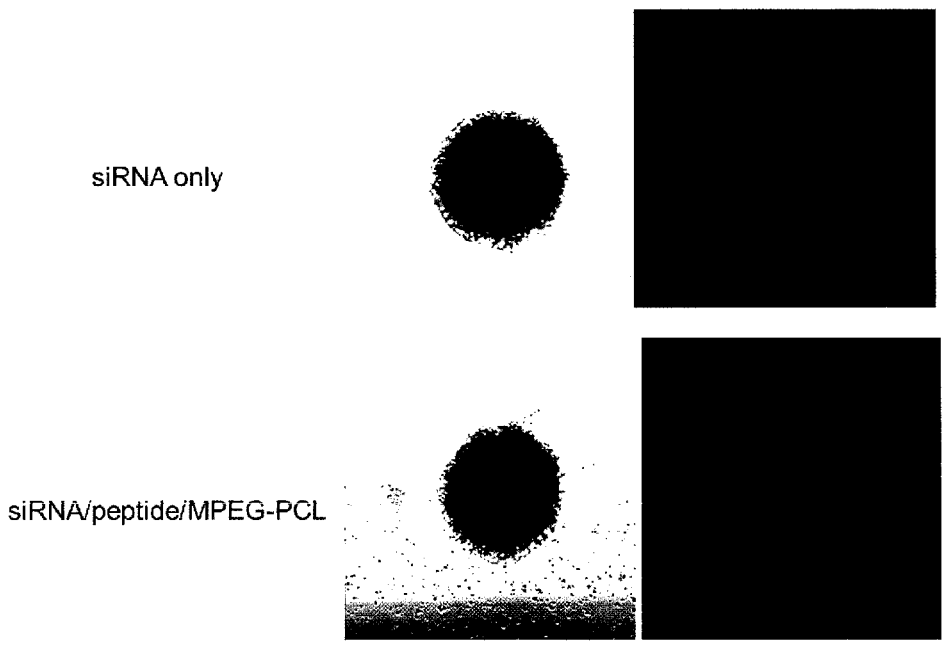
FIG. 14 is a confocal laser micrograph showing spheroid permeability of the nucleic acid-containing composition according to the present embodiment in mouse breast cancer cells.

The results are shown in FIG. 14. Incidentally, in FIG. 14, "siRNA only" means a system to which the above-mentioned FAM-siRNA (Cont1) alone was added, "siRNA+peptide+MPEG-PCL" means a system to which the nucleic acid-containing composition of the present invention (a complex (similar to Example 10) in which the above-mentioned FAM-siRNA (Cont1), the peptide having a sequence represented by STR-CHHRRRRHHC and MPEG-PCL (2000-2000) were mixed) was added.

As shown in FIG. 14, t was shown that permeability to spheroids was low in siRNA alone. On the other hand, the nucleic acid-containing composition of the present invention showed high permeability to spheroids.

«Test Group D-2: In Vitro Evaluation Intracellular Uptake Efficiency2»

$1 \times 10^5$ cells of mouse breast cancer cells of 4T1 cells were suspended in 10 mL of RPMI1640 medium (containing 10% FBS, 1% penicillin and 1% streptomycin), seeded in a flask for cell culture, and cultured at 37° C. under 5% carbon dioxide conditions. The cultured 4T1 cells (about 80% confluent) were washed with PBS twice, detached from the flask by 0.25% trypsin-EDTA solution, and 10% FBS-containing RPMI1640 medium was added to make a cell suspension with $1 \times 10^5$ cells/mL. This was seeded to 24 well plate per 1 mL each, and cultured for 24 hours and washed with PBS twice. Thereafter, it was changed with 900 µL of RPMI1640 medium of FBS(−), in the same method as in Example 10, each sample (N/P ratio is 10) containing FAM-siRNA (Cont1) was added so that FAM-siRNA (Cont1) became 100 nM per 1 well (transfection) and cultured at 37° C. under 5% carbon dioxide conditions for 6 hours. After transfection, the cells were washed with PBS twice, 300 µL of 0.25% trypsin-EDTA solution was added and the cells were cultured at 37° C. under the conditions of 5% carbon dioxide for 5 minutes. The cells were detached by adding 700 µL of a medium (FBS(+): the above-mentioned 10% FBS-containing RPMI1640), the detached cell suspension was recovered in an Eppendorf tube, and after centrifugation, the supernatant was aspirated and washed with PBS (1 mL) once and centrifuged. After removing the supernatant by suction, PBS (500 µL) was added, and the mixture was filtered through a 200-mesh nylon net to remover a cell suspension. This cell suspension was measured by Flow Cytometry (FACS Canto, Becton Dickinson) to evaluate the efficiency of uptake of the cells. On a plot showing a side scattered light to a forward scattered light, the cell population was gated, and in a plot of the cell number against the fluorescence intensity in the control of the target cell group, the range containing 95% of the cells was defined to be a P1 region, and the range where the fluorescence intensity was stronger than that was defined to be a P2 region. When FAM-siRNA (Cont1) was taken into cells, the number of cells in the P2 region increases, so that a ratio of cells contained in the P2 region of the cell population was used as an index of the amount of FAM-siRNA (Cont1) taken into the cells.

As a control, using a system in which FAM-siRNA (Cont1) alone was added at the time of transfection, and LipoTrust (Registered Trademark) EX Oligo (manufactured by Hokkaido System Science Co., Ltd.) which is a kit containing a gene or nucleic acid introducing reagent, a system according to the protocol of the kit was simultaneously carried out.

Figure 15:
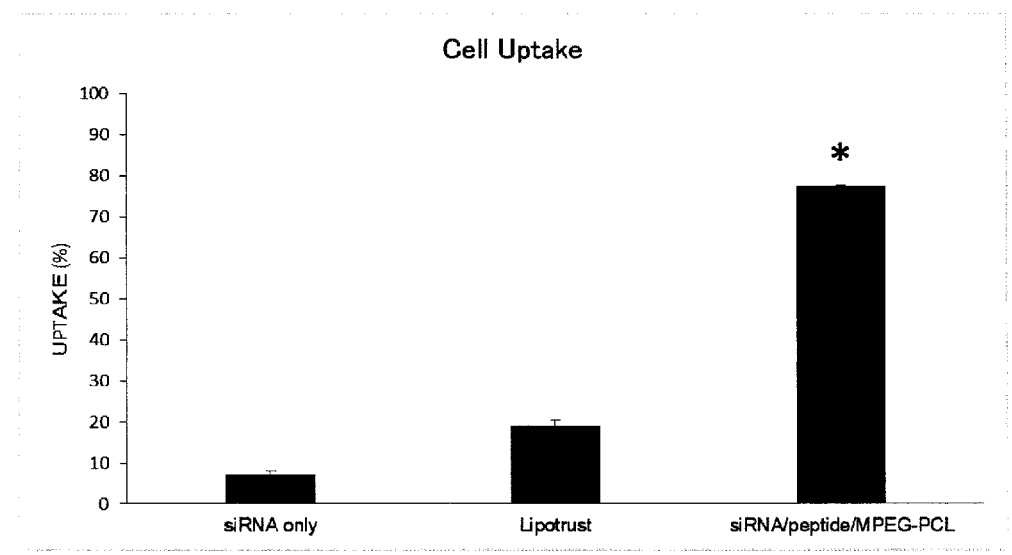
FIG. 15 is a graph showing an intracellular introduction rate of the nucleic acid-containing composition according to the present embodiment in mouse breast cancer cells.

Each group was carried out with n=8. The results are shown in FIG. 15. Incidentally, in FIG. 15, "siRNA only" means a system to which the above-mentioned FAM-siRNA (Cont1) alone was added, "LipoTrust" means a system according to the protocol of the kit using the above-mentioned LipoTrust (Registered Trademark) EX Oligo, "siRNA+peptide+MPEG-PCL" means a system to which the nucleic acid-containing composition of the present invention (a complex same as in Example 10) in which the above-mentioned FAM-siRNA(Cont1), the peptide having a sequence represented by STR-CHHRRRRHHC and MPEG-PCL(2000-2000) were mixed) was added, "Cell Uptake" means a cell introducing ratio, and "Uptake" means an introducing ratio. In FIG. 15, an average value of the introducing ratio is shown and the error bars indicate standard deviation. The P value (Dunnett test) compared with the LipoTrust group is indicated by the number of *, and * is P<0.001.

As shown in FIG. 15, in the nucleic acid-containing composition of the present invention, the uptake in the cells was about 80% at 6 hours after transfection, and the introducing ability into the cells were confirmed to be sufficient.

UTILIZABILITY IN INDUSTRY

According to the present invention, there are provided a composition for delivering a nucleic acid and a nucleic acid-containing pharmaceutical composition that achieve low cytotoxicity and high therapeutic efficacy. Such a composition can be used, for example, as a pharmaceutical composition for therapy, and its industrial value is extremely large, and it is possible to provide a nucleic acid therapeutic agent for controlling a disease-causing molecule to obtain a therapeutic effect.

The disclosure of Japanese Patent Application No. 2017-135547 (filing date: Jul. 11, 2017) is incorporated herein by reference in its entirety. All documents, patent applications, and technical standards mentioned in the present specification are to the same extent as if each individual document, patent application, and technical standard were specifically and individually stated to be incorporated in the present specification by reference.

The invention claimed is:

1. A composition for delivering a nucleic acid which comprises a block copolymer in which a polyethylene glycol segment and a hydrophobic polyester segment are linked, and a peptide having 4 to 30 residues containing at least one amino acid selected from the group consisting of arginine and lysine, wherein the block copolymer and the peptide are not conjugated to each other via a covalent bond.

2. The composition for delivering a nucleic acid according to claim 1, wherein the peptide contains a fat-soluble group directly or through a bonding group.

3. The composition for delivering a nucleic acid according to claim 2, wherein the fat-soluble group is a group selected from the group consisting of a (C4 to C30) linear, branched or cyclic alkyl group which may have a substituent(s), a (C4 to C30) linear, branched or cyclic alkenyl group which may have a substituent(s) and a (C7 to C30) linear or branched aralkyl group which may have a substituent(s).

4. The composition for delivering a nucleic acid according to claim 1, wherein the peptide further contains histidine.

5. The composition for delivering a nucleic acid according to claim 1, wherein the peptide contains arginine and histidine.

6. The composition for delivering a nucleic acid according to claim 5, wherein a total number of an arginine residue and a histidine residue in the peptide is 50 to 100% of a total number of all residues of the peptide.

7. The composition for delivering a nucleic acid according to claim 1, wherein the block copolymer is a polyethylene glycol-poly(ε-caprolactone), a polyethylene glycol-poly(lactic acid-glycolic acid copolymer) or a polyethylene glycol-polylactic acid.

8. The composition for delivering a nucleic acid according to claim 1, wherein the block copolymer is a polyethylene glycol-poly(ε-caprolactone).

9. The composition for delivering a nucleic acid according to claim 1, wherein the block copolymer and the peptide form a particle.

10. The composition for delivering a nucleic acid according to claim 9, wherein a particle size of the particle is 50 nm or less.

11. A method for manufacturing the composition for delivering a nucleic acid according to claim 1, which comprises the steps of mixing a water-soluble organic solvent solution of a block copolymer in which a polyethylene glycol segment and a hydrophobic polyester segment are linked, and an aqueous solution of a peptide having 4 to 30 residues containing at least one amino acid selected from the group consisting of arginine and lysine, and then, removing the organic solvent.

12. A nucleic acid-containing composition which comprises the composition for delivering a nucleic acid according to claim 1 contains a nucleic acid.

13. The nucleic acid-containing composition wherein the composition for delivering a nucleic acid according to claim 9 is a nucleic acid-containing composition containing a nucleic acid, and the nucleic acid forms a particle with the block copolymer and the peptide.

14. The nucleic acid-containing composition according to claim 13, wherein a particle size of the particle is 50 nm or less.

15. The nucleic acid-containing composition according to claim 12, wherein the nucleic acid is RNA utilizing RNA interference or an antisense nucleic acid.

16. The nucleic acid-containing composition according to claim 12, wherein the nucleic acid is siRNA or miRNA.

17. A method for manufacturing the nucleic acid-containing composition according to claim 12, which comprises the steps of mixing a water-soluble organic solvent solution of a block copolymer in which a polyethylene glycol segment and a hydrophobic polyester segment are linked, and an aqueous solution of a peptide having 4 to 30 residues and containing at least one amino acid selected from the group consisting of arginine and lysine, and after removing the organic solvent, mixing a nucleic acid(s).

18. A nucleic acid-containing composition wherein the nucleic acid-containing composition according to claim 12 further contains a low-molecular weight drug.

19. A kit for delivering a nucleic acid which comprises the composition for delivering a nucleic acid according to claim 1.

20. A kit for delivering a nucleic acid which comprises a first composition containing a block copolymer in which a polyethylene glycol segment and a hydrophobic polyester segment are linked, and a second composition containing a peptide having 4 to 30 residues containing at least one amino acid selected from the group consisting of arginine and lysine.

21. A pharmaceutical composition which comprises the nucleic acid-containing composition according to claim 12 as an effective ingredient.

* * * * *